United States Patent
Kato et al.

(10) Patent No.: US 10,271,500 B2
(45) Date of Patent: Apr. 30, 2019

(54) ONION WITH REDUCED PUNGENCY THAT DOES NOT GENERATE LACHRYMATORY COMPONENT

(71) Applicant: HOUSE FOODS GROUP INC., Higashiosaka-shi, Osaka (JP)

(72) Inventors: Masahiro Kato, Osaka (JP); Jinji Shono, Osaka (JP); Noriya Masamura, Osaka (JP); Shinsuke Imai, Osaka (JP); Yasuhiro Kamata, Osaka (JP)

(73) Assignee: HOUSE FOODS GROUP INC., Higashiosaka-shi (JP)

( * ) Notice: Subject to any disclaimer, the term of this patent is extended or adjusted under 35 U.S.C. 154(b) by 0 days.

(21) Appl. No.: 14/888,296

(22) PCT Filed: May 1, 2014

(86) PCT No.: PCT/JP2014/062059
§ 371 (c)(1),
(2) Date: Oct. 30, 2015

(87) PCT Pub. No.: WO2014/178420
PCT Pub. Date: Nov. 6, 2014

(65) Prior Publication Data
US 2016/0073607 A1   Mar. 17, 2016

(30) Foreign Application Priority Data

May 1, 2013   (JP) ................. 2013-096551

(51) Int. Cl.
*A01H 5/12* (2018.01)
*C12Q 1/527* (2006.01)
*C12N 15/01* (2006.01)
*A01H 5/04* (2018.01)

(52) U.S. Cl.
CPC ............. *A01H 5/12* (2013.01); *A01H 5/04* (2013.01); *C12N 15/01* (2013.01); *C12Q 1/527* (2013.01)

(58) Field of Classification Search
None
See application file for complete search history.

(56) References Cited

U.S. PATENT DOCUMENTS 7,452,988 B2 *   11/2008   Imai .................. C12N 9/90
                                                            435/320.1

FOREIGN PATENT DOCUMENTS

| JP | 2009-501528 A | 1/2009 |
| JP | 2011-510618 A | 4/2011 |
| WO | WO 2007/011857 A2 | 1/2007 |
| WO | WO 2009/092560 A1 | 7/2009 |

OTHER PUBLICATIONS

Eady et al., 2005, Acta Hort. 688: 181-188.*
Onion (Allium cepa) alliinase, GenBank Accession No. AAA32639. 1, published Apr. 27, 1993.*
Joshi et al., 2011, International Journal of Botany 7: 243-248.*
Tao et al., 2008, Cell 133: 164-176.*
Clark, 1993, PhD thesis, University of Canterbury, Christchurch, New Zealand, pp. 1-225.*
Eady et al., "Transgenic Onions with Reduced Alliinase Activity: Biochemical and Molecular Assessment", Acta Horticulturae, vol. 688, 2005, pp. 181-188.
Gilpin et al., Nucleotide sequence of a nuclear clone of alliinase (Accession No. L48614) from onion (PGR95-125), Plant Physiol., vol. 110, 1996, p. 336.
Imai et al., "An onion enzyme that makes the eyes water", Nature, vol. 419, No. 6908, Oct. 17, 2002, p. 685.
International Search Report issued in PCT/JP2014/062059, dated Jun. 17, 2014.
Written Opinion issued in PCT/JP2014/062059, dated Jun. 17, 2014.

* cited by examiner

*Primary Examiner* — Bratislav Stankovic
(74) *Attorney, Agent, or Firm* — Birch, Stewart, Kolasch & Birch, LLP

(57) ABSTRACT

This invention provides an onion exhibiting very weak or no pungency and a method for producing such onion. In such onion, alliinase gene expression is reduced.

4 Claims, 12 Drawing Sheets
Specification includes a Sequence Listing.

Fig. 11

| Gene No. | Expression level | | | | | | p-value | FDR | Results of annotation | Sequence identity with Gene 1 (%) |
|---|---|---|---|---|---|---|---|---|---|---|
| | #6-1 | #6-2 | #6-3 | Control 1 | Control 2 | Control 3 | | | | |
| 1 | 0.03 | 0.09 | 0.01 | 1066.44 | 120.36 | 68.41 | 2.9E-15 | 2.0E-12 | Alliinase | |
| 2 | 0.50 | 0.47 | 0.58 | 0.53 | 0.04 | 0.00 | 4.3E-01 | 1.0E+00 | Alliinase-like | 62.8 |
| 3 | 0.01 | 0.15 | 0.00 | 0.03 | 0.00 | 0.00 | 3.2E-01 | 8.9E-01 | Alliinase-like | 62.5 |
| 4 | 0.00 | 0.00 | 0.00 | 0.00 | 0.06 | 0.00 | 1.1E-01 | 5.4E-01 | Alliinase-like | 62.5 |
| 5 | 0.33 | 0.00 | 0.25 | 0.72 | 0.27 | 0.52 | 1.6E-01 | 6.7E-01 | Alliinase-like | 57.0 |
| 6 | 0.00 | 0.00 | 0.00 | 0.00 | 0.05 | 0.00 | 2.2E-01 | 7.7E-01 | Alliinase-like | 56.8 |
| 7 | 0.12 | 0.01 | 0.10 | 0.28 | 0.00 | 0.06 | 5.3E-01 | 1.0E+00 | Alliinase-like | 56.8 |
| 8 | 1.72 | 1.06 | 0.97 | 1.16 | 1.33 | 1.83 | 5.4E-01 | 1.0E+00 | Alliinase-like | 47.0 |
| 9 | 4.48 | 4.66 | 4.29 | 3.86 | 4.28 | 3.77 | 8.9E-01 | 1.0E+00 | Alliinase-like | 46.1 |
| 10 | 0.85 | 0.81 | 0.94 | 0.83 | 0.34 | 1.62 | 6.9E-01 | 1.0E+00 | Alliinase-like | 41.9 |
| 11 | 0.00 | 0.00 | 0.00 | 0.00 | 0.00 | 0.00 | 1.0E+00 | 1.0E+00 | Alliinase-like | 32.1 |
| 12 | 11.53 | 10.46 | 7.83 | 12.12 | 22.63 | 18.87 | 1.1E-01 | 5.4E-01 | Alliinase-like | 31.7 |
| 13 | 0.00 | 0.00 | 0.00 | 0.48 | 0.00 | 0.00 | 3.5E-02 | 2.7E-01 | Alliinase-like | 30.7 |
| 14 | 0.39 | 0.39 | 0.17 | 0.00 | 0.17 | 0.28 | 4.5E-01 | 1.0E+00 | Alliinase-like | 30.5 |
| 15 | 2.36 | 2.14 | 2.94 | 1.15 | 2.86 | 3.12 | 8.4E-01 | 1.0E+00 | Alliinase-like | 27.3 |
| 16 | 0.00 | 0.00 | 0.00 | 0.18 | 0.00 | 0.00 | 1.5E-01 | 6.5E-01 | Alliinase-like | 25.5 |
| 17 | 4.86 | 4.43 | 5.14 | 8.32 | 11.59 | 11.48 | 4.1E-02 | 3.0E-01 | Alliinase-like | 21.0 |
| 18 | 1.42 | 0.92 | 1.16 | 1.32 | 1.44 | 2.46 | 2.9E-01 | 8.7E-01 | Alliinase-like | 16.9 |
| 19 | 0.00 | 0.00 | 0.34 | 0.00 | 0.00 | 0.00 | 2.3E-01 | 7.8E-01 | Alliinase-like | 16.1 |
| 20 | 0.00 | 0.06 | 0.13 | 0.01 | 3.59 | 4.60 | 9.9E-04 | 2.0E-02 | Alliinase-like | 15.5 |
| 21 | 0.00 | 0.00 | 0.00 | 0.13 | 0.00 | 0.14 | 8.9E-02 | 4.9E-01 | Alliinase | 15.3 |
| 22 | 0.00 | 0.00 | 0.13 | 0.00 | 0.25 | 0.23 | 3.6E-01 | 9.1E-01 | Alliinase precursor | 14.8 |
| 23 | 0.05 | 0.00 | 0.56 | 10.54 | 0.05 | 0.11 | 1.8E-02 | 1.8E-01 | Alliinase-like | 14.3 |
| 24 | 3.98 | 4.55 | 5.19 | 0.56 | 0.00 | 0.00 | 1.8E-03 | 3.1E-02 | Alliinase-like | 14.1 |
| 25 | 0.21 | 0.00 | 0.00 | 0.46 | 0.00 | 0.21 | 3.3E-01 | 8.9E-01 | Alliinase-like | 13.7 |
| 26 | 0.00 | 0.00 | 0.00 | 0.13 | 0.39 | 0.00 | 3.7E-02 | 2.8E-01 | Alliinase-like | 13.7 |
| 27 | 0.00 | 0.00 | 0.00 | 0.29 | 0.05 | 0.16 | 2.5E-02 | 2.2E-01 | Alliinase-like | 12.9 |
| 28 | 0.00 | 0.00 | 0.00 | 0.56 | 0.00 | 0.25 | 8.5E-02 | 4.7E-01 | Alliinase-like | 9.4 |
| 29 | 0.53 | 0.87 | 0.77 | 0.68 | 1.79 | 1.57 | 2.3E-01 | 7.9E-01 | Alliinase-like | 9.2 |

Fig. 12

Alliinase amino acid sequence encoded by alliinase gene 1 (SEQ ID NO: 5)

MESYHKVGSNKMPSLLILICIIMSSFVNNNIAQAKVTWSLKAAEEAEAVANINCSGHGRAFLDGILSDGSPKCECNT
CYTGADCSEKITGCSADVASGDGLFLEEYWQQHKENSAVLVSGWHRMSYFFNPVSNFISFELEKTIKELHEIVGNAA
AKDRYIVFGVGVTQLIHGLVISLSPNMTATPCAPQSKVVAHAPYYPVFREQTKYFDKKGYEWKGNAADYVNTSTPEQ
FIEMVTSPNNPEGLLRHEVIKGCKSIYDMVYYWPHYTPIKYKADEDIMLFTMSKYTGHSGSRFGWALIKDETVYNKL
LNYMTKNTEGTSRETQLRSLKILKEVIAMVKTQKGTMRDLNTFGFQKLRERWVNITSLLDKSDRFSYQKLPQSEYCN
YFRRMRPPSPSYAWVKCEWEEDKDCYQTFQNGRINTQSGEGFEAGSRYVRLSLIKTKDDFDQLMYYLKNMVEAKRKT
PLIKQLSNDQISRRPFI

ONION WITH REDUCED PUNGENCY THAT DOES NOT GENERATE LACHRYMATORY COMPONENT

TECHNICAL FIELD

The present invention relates to an onion exhibiting very weak or no pungency and tear-inducing property and a method for producing such onion.

BACKGROUND ART

In recent years, trends toward the provision of vegetables that children can easily eat or the intake of raw vegetables by health-conscious consumers become popular, and an attempt of improvement of vegetable varieties is made to satisfy such needs. However, vegetables, such as plants of the genus *Allium*, in particular, onions, are difficult to eat raw because of distinctive pungency.

The lachrymatory factor (LF) serving as a pungent component and also as a lachrymatory component of an onion are found to be generated by the reaction mechanism shown below, which proceeds upon cutting or breaking of raw onion tissue (Imai S. et al., An onion enzyme that makes the eyes water, Nature, 419, 685, 2002).

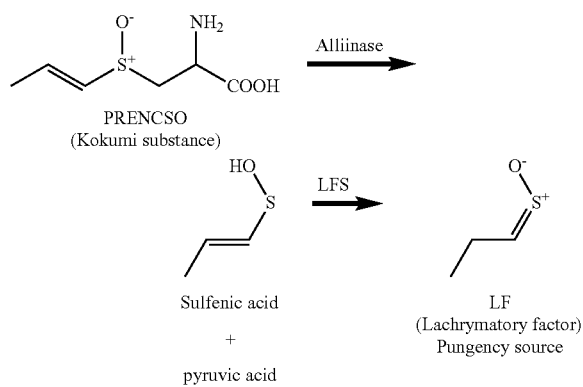

When onion cell is broken upon cooking or processing, specifically, trans-1-propenyl cysteine sulfoxide (PRENCSO) as a substrate is degraded by alliinase, and sulfenic acid (1-propenyl sulfenic acid), pyruvic acid, and ammonia are generated in an amount of a molecule each from a molecule of PRENCSO. The generated sulfenic acid is then converted into a lachrymatory factor (LF, propanethial-S-oxide) as a pungent component by lachrymatory factor synthase (LFS).

In Japan, there is a very early maturing variety of an onion with low pungency, which is referred to as "spring onion." In a very early maturing onion variety, moisture content is high and the amount of dry matter is low. The PRENCSO concentration is lowered and the amount of a pungent component (a lachrymatory factor) generated is reduced because of the features described above. While pungency of a very early maturing onion variety is low, it yields some pungency. Accordingly, it is necessary to immerse an onion in water when it is to be eaten raw. In addition to a labor required for immersion of an onion in water, nutritious components would be lost due to immersion. Also, the storage stability of the variety indicated above is poor and, disadvantageously, such variety can be provided only at the limited time.

As a technique of producing a variety with low pungency, a technique of regulating fertilization to reduce the amount of a substrate serving as an origin of pungency has been employed. However, such substrate is not completely eliminated by the technique, and, in general, pungency would not be reduced to an extent that pungency is not sensed when an onion is eaten raw.

In addition, onions with reduced pungency have heretofore been developed and reported. JP 2009-501528 A discloses long-day onions having low pungency and the amount of pyruvic acid generated when the onion tissues are broken is 3.0 to 5.5 µmol/g. JP 2011-510618A also discloses long-day onions having low pungency and the amount of pyruvic acid generated when the onion tissues are broken is 2.5 to 5.5 µmol/g FW. While the onion varieties disclosed therein exhibit low pungency, such onions are not completely free of pungency. Accordingly, it is necessary to immerse such onions in water when they are to be eaten raw.

Accordingly, onions with very weak or no pungency and tear-inducing property are still desired in the art.

SUMMARY OF THE INVENTION

Objects to Be Attained by the Invention

It is an object of the present invention to provide an onion with very weak or no pungency and tear-inducing property and a method for producing such onion.

Means for Attaining the Objects

The present inventors have conducted concentrated studies in order to attain the above objects. As a result, they discovered that the alliinase gene expression may be reduced in onion cells, so as to produce onions with very weak or no pungency and tear-inducing property. This has led to the completion of the present invention.

Specifically, the present invention has the following features.

[1] An onion plant or an offspring or a part thereof in which alliinase gene expression is reduced compared with the case of an existing variety.

[2] The onion plant or an offspring or a part thereof according to [1], wherein amounts of a pungent and a lachrymatory component produced when an onion cell is broken are decreased compared with the case of an existing variety.

[3] The onion plant or an offspring or a part thereof according to [1] or [2], wherein the alliinase gene comprises a nucleotide sequence encoding any of the following polypeptides (a) to (c):

(a) a polypeptide comprising the amino acid sequence as shown in SEQ ID 5;

(b) a polypeptide comprising an amino acid sequence having one or a plurality of amino acid deletion, substitution, insertipn, and/or addition in the amino acid sequence as shown in SEQ ID NO: 5 and having alliinase activity; and (c) a polypeptide comprising an amino acid sequence exhibiting 90% Or higher identity to the amino acid sequence as shown in SEQ. ID NO: 5 and having alliinase activity.

[4] A method for producing an onion plant or a part thereof in which alliinase gene expression is reduced compared with the case of an existing variety, the method comprising the following steps:

(i) inducing mutagenesis in an onion seed;

(ii) cultivating the mutagenized onion seed so as to obtain an onion plant or apart thereof; and (iii) selecting an onion plant or a part thereof exhibiting one or more traits described below from the obtained onion plant or a part thereof;
  a) the amounts of a pungent and a lachrymatory component produced when an onion cell is broken are decreased compared with the case of an existing variety;
  b) alliinase gene or protein expression is reduced compared with the case of an existing variety;
  c) the amount of pyruvic acid produced when an onion cell is broken is decreased compared with the case of an existing variety;
  d) the amount of PRENCSO remaining after an onion cell is broken is increased compared with the case of an existing variety; and
  e) the amount of a lachrymator factor (LF) produced when an onion cell, is broken is decreased compared with the case of an existing variety.

[5] The method according to [4], wherein the step (iii) comprises selecting an onion plant or a part thereof exhibiting at least the trait (b).

[6] The method according to [4], which further comprises a step (iv) of allowing the selected onion plant to undergo self-fertilization and subjecting the obtained onion plant or a part thereof to the step (iii), which is carried out once or a plurality of times.

[7] The onion plant or an offspring or a part thereof according to [1], wherein the part of the onion plant is a seed deposited internationally under NCIMB 42219.

[8] The onion plant or an offspring or a part thereof according to [I], wherein the part of the onion plant is a callus deposited internationally under FERM BP-22260.

[9] An onion plant or a part thereof in which alliinase gene expression is reduced compared with the case of an existing variety, which is produced by a method comprising the following steps:
  (i) inducing mutagenesis in an onion seed;
  (ii) cultivating the mutagenized onion seed so as to obtain an onion plant or a part thereof; and
  (iii) selecting an onion plant or a part thereof exhibiting one or more traits described below from the obtained onion plant or a part thereof:
    a) the amounts of a pungent and a lachrymatory component produced when an onion cell is broken are decreased compared with the case of an existing variety;
    b) alliinase gene or protein expression is reduced compared with the case of an existing variety;
    c) the amount of pyruvic acid produced when an onion cell is broken is decreased compared with the case of an existing variety;
    d) the amount of PRENCSO remaining after an onion cell is broken is increased compared with the case of an existing variety; and
    e) the amount of a lachrymatory factor (LF) produced when an onion cell is broken is decreased compared with the case of an existing variety.

[10] The onion plant or a part thereof according to [9], wherein the step (iii) comprises selecting an onion plant or a part thereof exhibiting at least the trait (b).

[11] The onion plant or a part thereof according to [9], Wherein the method further comprises a step (iv) of allowing the selected onion plant to undergo self-fertilization and subjecting the obtained onion plant to the step (iii), which is carried out once or a plurality of times.

[12] A method for producing an onion plant or a part thereof in which alliinase gene expression is reduced compared with the case of an existing variety,
the method Comprising crossing a first onion plant in which alliinase gene expression is reduced compared with the case of an existing variety with a second onion plant.

[13] An onion plant or a part thereof in which alliinase gene expression is reduced compared with the case of an existing variety, which is produced by the method comprising crossing a first onion plant in which alliinase gene expression is reduced compared with the case of an existing variety with a second onion plant.

[14] An onion plant or an offspring or a part thereof obtained from a part of the onion plant in which alliinase gene expression is reduced compared with the case of an existing variety.

[15] The onion plant or an offspring or a part thereof according to [14] obtained from a seed or a callus of the onion plant in which alliinase gene expression is reduced compared with the case of an existing variety.

[16] The onion plant or an offspring or a part thereof according to [15], wherein the seed is deposited internationally under NCIMB 42219.

[17] The onion plant or an offspring or a part thereof according to [15], wherein the callus is deposited internationally under FERM BP-22260.

[18] A method of evaluating the pungency of an onion plant or a part thereof, which comprises assaying the level of alliinase gene expression in the Onion plant or the part thereof.

[19] A method for selecting an onion plant in which the amounts of a pungent and a lachrymatory component produced are decreased compared with the case of an existing variety or a part thereof,
the method comprising assaying the level of alliinase gene expression in an onion plant or a part thereof and selecting the onion plant or a part thereof in which alliinase gene expression is reduced compared with the case of an existing variety.

This description includes part or all of the content as disclosed in the description and/or drawings of Japanese Patent Application No. 2013-096551, which is a priority document of the present application.

Effects of the Invention

The present invention can provide an onion with very weak or no pungency and tear-inducing property and a method for producing such onion.

BRIEF DESCRIPTION OF THE DRAWINGS

FIG. 11 shows the results of alliinase gene expression analysis and annotation of the onion bulb of the line #6 and a control onion bulb.

FIG. 12 shows an amino acid sequence encoded by the alliinase gene that is suppressed to express in an onion bulb of the line #6 at a significant level.

EMBODIMENTS FOR CARRYING OUT THE INVENTION

Figure 1:
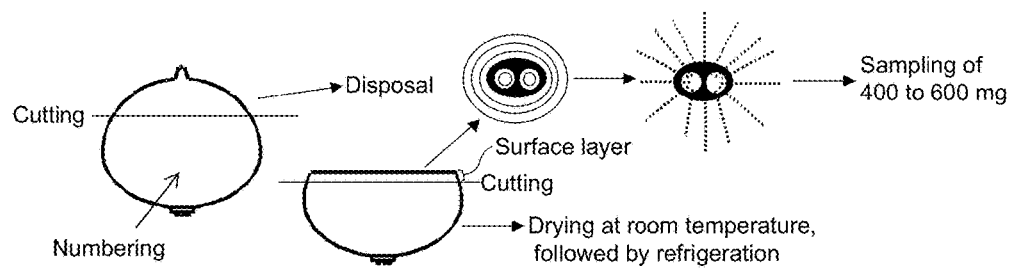
FIG. 1 schematically shows a method for obtaining an analyte sample from an onion bulb.

1. The Onion of the Present Invention

In the onion of the present invention, alliinase gene expression is reduced.

The term "onion plant" used herein refers to an onion plant and apart of the plant, unless otherwise specified. A "part of the plant" refers to any of a seed, bulb, scale leaf, leaf, stem, bud, flower, anther, pollen, or ovule of an onion, and a cell, tissue, protoplast, or callus derived therefrom, unless otherwise specified. An example of an onion seed is one deposited internationally under Accession Number: NCIMB 42219, and an example of an onion callus is one deposited internationally under Accession Number: FERM BP-22260. A bulb or scale leaf of an onion is occasionally referred to simply as an "onion" herein, and these terms are interchangeably used.

In the present invention, an "offspring" of an onion plant s an onion plant having a history of being produced from the onion plant of the present invention or a part thereof by means of sexual reproduction and/or asexual reproduction. In such onion plant, alliinase gene expression is reduced compared with the case of existing varieties.

The onion plant of the present invention and an offspring thereof can be cultivated in accordance with a general technique relevant for the variety used, and such plants can be seed-propagated. It is generally known that a callus can be induced from apart of a plant tissue. A callus induced in such a procedure can be easily regenerated by regulating a composition of a culture medium or culture conditions. Thus, a plant regenerated in such a procedure does not differ from a plant grown from a seed in terms of traits. Such properties are applicable to onions, plants can be regenerated from calluses prepared from the growing point of a bulb, pollens, ovules, anthers, or seedlings, and plants regenerated in such a procedure or seeds obtained therefrom have the same traits as those of plants grown from seeds or seeds obtained from, such plants.

The term "onion cell" used herein refers to a cell contained in an onion plant, and preferably a cell contained in an onion bulb or onion scale leaf.

The term "alliinase gene" used herein is a collective designation for a plurality of alliinase genes including one or more single nucleotide polymorphism(s) (SNP(s)), unless otherwise specified.

In the present invention, the term "alliinase gene" preferably refers to a particular alliinase gene that is mainly influential on the production of a pungent and a lachrymatory component. Such particular alliinase gene is identified by the following step: (Step 1) selecting an onion in which the amount of a pungent and a lachrymatory component produced is reduced by one or more evaluation and assay techniques selected from among functional evaluation, an assay of the amount of pyruvic acid production, an assay of the amount of remaining PRENCSO, and an assay of the amount of LF production described below; (Step 2) exhaustively analyzing alliinase gene expression in the selected onion and in a control onion of the same variety, which has pungency, using a next-generation sequencer by the technique described in detail in Example 7, so as to, extract a gene sequence exhibiting a difference in the gene expression level between the test onion and the control onion; and, (Step 3) when the alliinase gene that is reduced to be expressed in the selected onion at a significant level and Observed- to be expressed in the control onion is found in the extracted gene sequence, identifying such alliinase gene as the particular alliinase gene. The expression level of the particular alliinase gene in the selected onion and the control onion (the selected onion: the control onion) may be, for example, 1:50 or more, preferably 0.1:100 or more, and more preferably 1:1000.

Such particular alliinase gene comprises or consists of a nucleotide sequence encoding any of the polypeptides (a) to (c):

(a) a polypeptide comprising or consisting of the amino acid sequence as shown in SEQ ID NO: 5;

(b) a polypeptide comprising or consisting of an amino acid sequence having one or a plurality of amino acid deletion, substitution, insertion, and/or addition in the amino acid sequence as shown in SEQ ID NO: 5 and having alliinase activity; or (c) a polypeptide comprising or consisting of an amino acid sequence exhibiting 70% or higher, 80% or higher, 90% or higher, 95% or higher, 96% or higher, 97% or higher, 98% or higher, or 99% or higher identity to the amino acid sequence as shown in SEQ ID NO: 5 and having alliinase activity.

The term "a plurality of" used herein refers to 10, 9, 8, 7, 6, 5, 4, 3, or 2. Amino acid sequences can be compared in accordance with a conventional technique, for example, with the use of BLAST (Basic Local Alignment Search Tool at the National Center for Biological Information) with default settings. The term "alliinase activity" refers to activity of degrading PRENCSO and generating sulfenic acid, pyruvic acid, and ammonia. The alliinase activity can be assayed in accordance with a technique described in detail in the examples below. It can be assayed by detecting and assaying a substance resulting from degradation of PRENCSO or a substance generated therefrom (i.e., sulfenic acid is converted into LF with the aid of LFS) via HPLC.

As a result of the searching by means of NCBI Protein Blast (with default parameters) using the amino acid sequence as shown in SEQ ID NO: 5 as a query sequence, SEQ ID NO: 5 was found to exhibit high homology of 99.8% (478a.a./479a.a.), 99.8%. (478a.a./479a.a.), and 98.7% (473a.a./479a.a.) to the sequences of Accession Numbers: AAA32639.1, AAA92463.1., and AAD26853.1, respectively.

When "alliinase gene expression is reduced compared with the case of an existing variety" in the present invention, the alliinase gene expression level in an onion cell is significantly lower than the alliinase gene expression level in a cell of an existing onion variety. For example, the expression level is less than one fiftieth, less than one hundredth, less than one two-hundredth, less than one three-hundredth, less than one four-hundredth, less than one five-hundredth, less than one six-hundredth, less than one seven-hundredth, less than one eight-hundredth, less than one nine-hundredth, less than one thousandth, less than one two-thousandth, less than one three-thousandth, less than one four-thousandth, less than one five-thousandth, less than one six-thousandth, less than one seven-thousandth, less than one eight-thousandth, less than one nine-thousandth, or less than one ten-thousandth or less. Such gene expression may or may not be lost.

The term "existing variety" used herein refers to a general onion variety that exhibits pungency and tear-inducing property when onion cells are broken. Examples thereof include known general spring-sown onion cultivars, such as Super Kita-momiji, Kita momiji 2000, Kita momiji, Sapporo-ki, Polestar, Tsuki hikari, Kitami-ki, Gekko No. 22, and Okhotsk, and autumn-sown onion cultivars, such as Osaka maw, Sen-nan Koudaka, Senshu Chu Kouki, Satsuki, and Moiniji, with Super Kita-momiji, Kita momiji 2000, and Sapporo-ki being preferable. Examples of existing varieties include onions in which the alliinase gene expression level is 40 or more, 50 or more, 60 or more, 70 or more, 80 or more, 90 or more, or 100 relative to the alliinase gene expression level in onions before mutagenesis, gene recombination, or hybridization (i.e., parent strains) and spring-sown onions, such as Super Kita-momiji, Kita momiji 2000, or Sapporo-ki, designated as 100. The term "existing variety" is hereinafter used in the same sense as described above.

Alliinase gene expression is reduced in the onion of the present invention compared with the case of existing varieties. Thus, PRENCSO contained in onion cells remains without being degraded or transformed by alliinase activity when onion cells are broken. As a result, the amounts of pyruvic acid and sulfenic acid produced are reduced, in comparison with the amounts thereof produced when onion cells derived from existing varieties are broken, and the amounts of LF, which are a pungent and a lachrymatory component, produced when LFS acts on sulfenic acid are reduced, in comparison with the amounts thereof produced when onion cells derived from existing varieties are broken. Accordingly, the onion of the present invention exhibits very weak or no pungency and tear-inducing property when onion cells are broken compared with the case of existing onion varieties. The amount of PRENCSO remaining in the onion of the present invention is preferably 2.0 µmol/g FW or more, more preferably 3.0 µmol/g FW or more, further preferably 4.0 µmol/g FW or more, and particularly preferably 5.0 µmol/g FW or more. In addition/Alternatively, the amount of pyruvic acid produced in the onion of the present invention is preferably 2.0 µmol/g FW or less, more preferably 1.5 µmol/g FW or less, further preferably 1.0 µmol/g/FW or less, and particularly preferably 0.5 µmol/g/FW or less. In addition/Alternatively, in the onion of the present invention, the amount of LF produced approximately 1 minute and 20 seconds after the onion cells are broken is preferably $1.0 \times 10^6$ peak area or less, more preferably $9.0 \times 10^5$ peak area or less, $8.0 \times 10^5$ peak area or less, $7.0 \times 10^5$ peak area or less, or $6.0 \times 10^5$ peak area or less, and further preferably $5.0 \times 10^5$ peak area or less, $4.0 \times 10^5$ peak area or less, $3.0 \times 10^5$ peak area or less, $2.0 \times 10^5$ peak area or less, or $1.0 \times 10^5$ peak area or less, relative to µl of the extract.

Since the onion of the present invention yields very weak or no pungency when onion cells are broken, compared with the case of existing onion varieties, adults and children who do not favor onion pungency are capable of eating such onions raw without immersing them in water. Because it is not necessary to immerse an onion in water before it is eaten raw, onion nutrients such as quercetin which is considered to be good for health would not escape into water, and nutrients can be efficiently ingested. Because it is not necessary to immerse an onion in water, a process of water immersion is not needed at factories where sliced onions are produced at the industrial level. This can reduce the production cost.

In addition, the onion of the present invention does not have tear-inducing property. This can significantly improve the conditions for cooking at home or operations at large-scale factories where peeled onions are produced.

Because the onion of the present invention yields very weak or no pungency, in addition, processed food raw materials that did not involve the use of onions in the past, such as non-heated vegetable raw materials (i.e., precut vegetables), heated vegetable raw materials (that enable preparation of fried sweet onions in a short period of time), and seasonings (PRENCSO, an amino acid, can enhance a flavor), can be easily prepared.

The amount of PRENCSO remaining when onion cells are broken is significantly larger in the onion of the present invention, compared with the case of existing onion varieties. PRENCSO is confirmed to have health functions (JP 2007-210918 A) and it is expected as a functional material. In case of existing onion varieties, however, PRENCSO is degraded and/or transformed during the process of cooking and processing. Accordingly, it was not easy to ingest PRENCSO by eating onions. In contrast, PRENCSO remains in the onion of the present invention without being degraded or transformed by alliinase activity. Thus, PRENCSO can be easily and efficiently ingested.

2. Method for Producing the Onion of the Present Invention

The onion of the present invention can be produced by a technique of mutagenesis or gene recombination.

According to a technique involving mutagenesis, onion seeds may be subjected to a known technique of mutagenesis (e.g., chemical processing using ethyl methanesulfonate (EMS) or physical processing using γ beams, X rays, or heavy ion beams). Any heavy ion beams can be used without particular limitation, provided that mutagenesis can be induced. Examples of heavy ion beams that can be used include nitrogen ion beams, carbon ion beams, neon ion beams, and argon ion beams. A heavy ion beam dose can be adequately determined in accordance with ion beam type to be employed or seed amount. It can be determined in accordance with a rate of germination from the irradiated seeds and a rate of normal growth thereof. Specifically, a dose that realizes a rate of germination of approximately 80% or higher and a rate of normal growth among the germinated plants of 50% or higher is preferable. In the case of the neon ion beam, for example, the heavy ion beam dose can be 5 to 50 Gy, preferably 10 to 40 Gy, and more preferably 20 to 30 Gy.

Varieties of onion seeds are not particularly limited, and seeds of existing varieties can be used.

Mutagenized, seeds are cultivated in accordance with a general procedure for onion cultivation and they are then allowed to form bulbs. The onion bulbs are subjected to the method of evaluation and selection described below so as to obtain the target onion bulb in which alliinase gene expression is reduced. The thus-selected onion bulbs are subjected to self-fertilization to obtain seeds, the resulting seeds are cultivated again, and onion bulbs resulting therefrom are then subjected to evaluation and selection. This procedure may be repeated more than one time, so as to obtain the target onion lines in which alliinase gene expression is stably reduced. Onion tissues subjected to evaluation and selection are not necessarily obtained from the formed onion bulbs, and tissues obtained from tissues other than bulbs such as growing leaves can be used.

According to a technique of gene recombination, a technique that can inhibit (or delete) alliinase gene expression may be employed. Examples of such technique include disruption of the alliinase gene and/or disruption of an alliinase gene expression regulatory region. The term "alliinase gene expression regulatory region" used herein refers to a region that regulates alliinase gene expression (transcription), and such region includes a promoter region and/or an enhancer region. The term "disruption" refers to introduction of a mutation into the alliinase gene and/or the alliinase gene expression regulatory region, so as to delete or inhibit alliinase gene expression. A mutation to be introduced into the alliinase gene and/or the alliinase gene expression regulatory region is not particularly limited, provided that it can result in deletion or inhibition of alliinase gene expression. A mutation can be introduced by substitution, deletion, insertion, and/or addition of one or more nucleotides. For example, a part of the alliinase gene and/or the alliinase gene expression regulatory region or the entire region thereof may be deleted. A mutation can be introduced into the alliinase gene and/or the alliinase gene expression regulatory region by a conventional technique involving homologous recombination. An example thereof is double crossover via homologous recombination. In short, the alliinase gene and/or the alliinase gene expression regulatory region derived from a host onion is cloned into a common vector known to a person skilled in the art, so as to introduce the gene. The alliinase gene region or the upstream region including the alliinase gene can be obtained by designing and synthesizing primers or probes in accordance with the nucleotide sequence information concerning the onion alliinase gene and screening for cDNA library or genome library derived from the host onion with the use of the primers or probes. Any vector generally known as a plant transformation vector may be used. For example, binary vectors or other types of vectors can be used. A binary vector contains two border sequences of approximately 25 bp of the right border (RB) and the left border (LB) of *Agrobacterium* T-DNA, and the alliinase gene and/or the alliinase gene expression regulatory region may be introduced into a region between the both border-sequences. A mutation is introduced into the nucleotide sequence of the cloned alliinase gene and/or the cloned alliinase gene expression regulatory region, so as to prepare a DNA construct containing the mutagenized alliinase gene and/or the mutagenized alliinase gene expression regulatory region. A mutation can be introduced by, for example, a PCR-based method. By introducing the DNA construct into a host onion, homologous recombination takes place between the mutagenized alliinase gene and/or the mutagenized alliinase gene expression regulatory region on the DNA construct and the alliinase gene and/or the alliinase gene expression regulatory region on the host chromosomes. Thus, the alliinase gene and/or the alliinase gene expression regulatory region of the host can be disrupted.

An example of a transformation technique comprising introducing the vector constructed as above into a host onion cell is a method involving the use of *Agrobacterium*. Alternatively, the vector can be introduced into a host cell by the gene gun method, electroporation, a method involving the use of a virus vector, the floral dip method, or the leaf disc method. The techniques of plant transformation or tissue culture are described in, for example, Ko Shimamoto, Kiyotaka Okada (ed.), Plant cell technology Series 15, Experimental protocol for model animals, From genetic technique to genomic analysis, Shujunsha, 2001.

According to a technique involving the use of the binary vector-*Agrobacterium* system, plant cells, calluses, or plant tissue sections are prepared and infected with *Agrobacterium*, so as to introduce the mutagenized alliinase gene and/or the mutagenized alliinase gene expression regulatory region into plant cells. At the time of transformation, a phenolic compound (acetosyringone) may be added to a medium, and such cells can be efficiently transformed in cases of monocotyledons, in particular.

More specifically, a solution of *Agrobacterium* is prepared, calluses or tissues (e.g., leaf sections, roots, stem sections, or growing points) of the host onion are immersed in the solution for several minutes, moisture is removed, and the resultant is subjected to co-culture on a solid medium. Calluses are plant cell masses and calluses can be induced from plant tissue sections or mature seeds with the use of a callus induction medium. The transformed calluses or tissue sections are selected, and the calluses can be regenerated into young plants in a regeneration medium. In the case of the tissue sections, calluses are induced from the tissue sections to regenerate into young plants. Alternatively, protoplasts may be prepared from the tissue sections, and regenerated into young plants via callus culture. The young plants thus obtained are transferred to soil, following rooting, so as to reproduce plants. Seeds can be obtained from such plants in accordance with common culture techniques (Tanikawa, T, Takagi, M., Ichii, M., 1996, Plant regeneration from suspension cultures of onion (*Allium cepa* L.), Plant Tissue Cult. Lett. 13: 259-264; Eady C C, 2002, Genetic Transformation of Onions, In: Rabinowitch H D, Currah L. (eds), *Allium* Crop Science: Recent Advances, CABI Publishing, New York, pp. 119-144).

When the floral dip method is employed, for example, a solution of *Agrobacterium* is prepared, floral buds of host onions that are grown to develop immature floral buds are immersed in the solution, the plants are allowed to grow in that state, and seeds are then harvested. The harvested seeds are sowed, the transformed plants are selected, and the selected plants are transferred to soil and allowed to grow therein. Thus, gene recombinant onion plants can be obtained. The onion plants thus obtained are cultivated in accordance with a conventional onion cultivation procedure and allowed to form bulbs. The resulting onion bulbs are subjected to the method of evaluation and selection described below, and target onion bulbs in which alliinase gene expression is reduced are obtained. The onion bulbs thus selected are allowed to self-fertilization, the resulting seeds are cultivated again, and the resulting onion bulbs are then evaluated and selected. By repeating such procedure more than one time, the target onion line in which alliinase gene expression is stably reduced can be obtained. Onion tissues subjected to evaluation and selection are not necessarily the formed onion bulbs, and tissues obtained from tissues other than bulbs, such as developing leaves, can be used.

3. Method of Onion Evaluation and Selection

Target onions in which alliinase gene expression is reduced can be selected from among the onions produced by the method described above and evaluated by the method described below.

(Preparation of Analyte Sample)

In order to avoid variations in the assay or evaluation results occurring due to the sites of plants used as analyte samples, the particular parts of plants described below are used as analyte samples. An onion bulb is divided into two on the plane perpendicular to the vertical axis of the bulb (i.e., the axis connecting the basal plate to the upper end of an onion bulb) by a distance that is ⅓ to ½ its height from the upper end of the onion bulb, and an analyte sample is obtained from a scale leaf at the center of the cut plane of the upper portion including the upper end or the lower portion including the basal plate (see FIG. 1). The "scale leaf at the center of the cut plane" is a surface layer of the cut plane of the innermost scale leaf appearing on the cut plane (a scale leaf surrounding a bud in the axial center) among the scale leaves in the vicinity thereof. The "surface layer" is, for example, a layer with a thickness of 2 mm to 10 mm from the cut plane. When individual plants are selected on the basis of the results of various measurements, it is preferable that an analyte sample be derived from a region other than the site including the growing point of the plant. For example, the basal plate of an onion bulb (scale leaves includes the growing point. By maintaining a site including the growing point, advantageously, the selected plant can be reproduced from such site.

A size of an analyte sample is not particularly limited, provided that the amount of the sample is sufficient for evaluation and assay.

An analyte sample can be broken using a micropestle or bead mill, according to need. Conditions for sample breaking can be determined by observing the configuration of the broken sample.

(Alliinase Gene or Protein Expression Level)

The alliinase gene expression level can be measured in accordance with a conventional technique used for nucleic acid quantification (e.g., Northern blotting or real-time PCR). Real-time PCR is preferably employed, Real-time PCR can be carried out with the use of cDNA synthesized from the analyte sample in accordance with a conventional technique. Any pair of primers can be used as long as the alliinase gene can be amplified, and the region to be amplified and the length thereof are not particularly limited, Real-time PCR can be carried out With the use of SYBR Green or fluorescent probes. A housekeeping gene type used for the correction of gene expression levels among samples is not particularly limited. For example, a ubiquitin gene can be used.

In the present invention, an onion in which the alliinase gene expression level is lower than the case of existing onion varieties can be evaluated and selected as a target onion in which alliinase gene expression is deleted or reduced. It is preferable to select an onion in which the alliinase gene expression level measured by the method described above is less than one fiftieth, less than one hundredth, less than one two-hundredth, less than one three-hundredth, less than one four-hundredth, less than one five-hundredth, less than one six-hundredth, less than one seven-hundredth, less than one eight-hundredth, less than one nine-hundredth, less than one thousandth, less than one two-thousandth, less than one three-thousandth, less than one four-thousandth, less than one five-thousandth, less than one six-thousandth, less than one seven-thousandth, less than one eight-thousandth, less than one nine-thousandth, or less than one ten-thousandth or less of the alliinase gene expression levels in existing onion varieties.

The alliinase protein expression level can be measured in accordance with a conventional technique used for protein quantification (e.g., Western blotting or enzyme-linked immunosorbent assay (ELISA)). ELISA is preferably employed. An anti-alliinase antibody used for ELISA may be a monoclonal or polyclonal antibody. The unpurified antiserum may be used as a polyclonal antibody, or a polyclonal antibody purified from the antiserum may be used. With the use of two types of monoclonal antibodies, alternatively, sandwich ELISA can be performed. Examples of animals to be immunized include rabbits, rats, goats, and chickens. Secondary antibodies comprising enzymes capable of detection, such as peroxidase or alkaline phosphatase, hound thereto can be used for detection via ELISA. A sample diluted to the quantifiable concentration is subjected to ELISA. An analyte sample is broken and a starting sample solution is extracted from the broken analyte sample with the use of an aqueous solvent. The starting solution is diluted 1,000 fold, preferably 10 to 1,000 fold, more preferably the starting solution is undiluted to 100 fold diluted, and further preferably undiluted to 50 fold diluted. An analyte sample obtained immediately after the sample is broken, to 3 hours thereafter can be used (the duration after the sample is broken is not particularly limited).

In the present invention, an onion in which the alliinase protein level is lower than the case of existing onion varieties can be evaluated and selected as a target onion in which alliinase gene expression is deleted or reduced. It is preferable to select an onion in which the alliinase protein expression level measured by the method described above is one thirtieth or less, more preferably one fiftieth or less, still more preferably one hundredth or less, further preferably one five-hundredth or less, and furthermore preferably one ten-hundredth or less, compared with the alliinase protein level in existing onion varieties measured in the same procedure.

When some or all of onion tissues are broken, PRENCSO, which is a substrate for a pungent component, is immediately degraded by alliinase, and sulfenic acid, which is a precursor for a pungent component, is produced. As described above, accordingly, an onion evaluated and selected on the basis of the alliinase gene or protein expression level has pungency and tear-inducing property occurring when onion cells are broken, which are significantly lower than those in general onion varieties. Therefore, pungency and tear-inducing property of an onion can be evaluated on the basis of the alliinase gene or protein expression level.

In addition to the method of evaluation and selection on the basis of the alliinase gene or protein expression level described above, the onion of the present invention can be selected by one or more methods of evaluation and assay described below on the basis of the amounts of a pungent and a lacluymatory component generated when some or all onion tissues are broken.

(Functional Evaluation)

Through functional evaluation, tear-inducing property sensed when a part of an analyte sample is broken or a degree of pungency sensed when an analyte sample is eaten is evaluated. In the present invention, an onion is evaluated and selected as a target onion in which pungency and/or tear-inducing property are reduced when 2 or more panels sense apparent reduction in pungency and/or tear-inducing property, compared with the case of existing onion varieties.

(Amount of Pyruvic Acid Production)

By measuring the amount of pyruvic acid produced when some or all onion tissues are broken, the degree of pungency of an onion from which an analyte sample is derived can be indirectly evaluated. The amount of pyruvic acid: produced can be determined by breaking the analyte sample, allowing the broken sample to react with dinitrophenylhydrazine immediately thereafter to 3 hours thereafter; and measuring the absorbance (515 nm) using a spectrophotometer. An analyte sample used is diluted to a quantifiable concentration, preferably the analyte sample is undiluted to 5-fold diluted. In the present invention, an onion can be evaluated and selected as having reduced pungency when the amount of pyruvic acid produced in the broken analyte sample is lower than the case of existing onion varieties. It is preferable to select an onion in which the amount of pyruvic acid produced which is measured by the method described above 2.0 μmol/g FW or less, more preferably 1.5 μmol/g FW or less, further preferably 1.0 μmol/g FW or less, and particularly preferably 0.5 μmol/g FW Or less.

(Amount of Remaining PRENCSO)

When some or all onion tissues are broken, a pungent component precursor, PRENCSO, is completely degraded into sulfenic acid, pyruvic acid, and ammonia by alliinase instantaneously. In general, accordingly, there should be no PRENCSO remaining in the broken onion tissue. By measuring the amount of PRENCSO in the solution containing the broken tissues (i.e., the amount of remaining PRENCSO) after a given period of time following onion tissue breaking, accordingly, alliinase activity can be indirectly assayed. The amount of remaining PRENCSO can be measured by breaking the analyte sample and subjecting the sample obtained 0.5 minutes to 3 hours, and preferably 3 hours thereafter to HPLC. In the present invention, an onion can be evaluated and selected as having reduced pungency or tear-inducing property when the amount of PRENCSO remaining after the analyte sample is broken is larger than the case of existing onion varieties. It is preferable to select an onion in which the amount of remaining PRENCSO measured by the method described above is 2.0 μmol/g FW or more, more preferably 3.0 μmol/g FW or more, further preferably 4.0 μmol/g FW or more, and particularly preferably 5.0 μmol/g FW or more.

(Amount of LF Production)

By measuring the amount of LF, a pungency and a lachrymatory component, produced when some or all onion tissues are broken, a degree of pungency and tear-inducing property of an onion from which an analyte sample is derived can be evaluated. The amount of LF produced can be measured by HPLC of a sample immediately to 3 minutes, and preferably 1 minute and 20 seconds after the analyte sample is broken. In the present invention, an onion can be evaluated and selected as having reduced pungency and tear-inducing property when the amount of LF produced in the broken analyte sample is smaller than the ease of existing onion, varieties. It is preferable to select an onion in which the amount of LF produced measured by the method described above is $1.0 \times 10^6$ peak area or less, more preferably $9.0 \times 10^5$ peak area or less; $8.0 \times 10^5$ peak area or less, $7.0 \times 10^5$ peak area or less, or $6.0 \times 10^5$ peak area or less, and further preferably $5.0 \times 10^5$ peak area or less, $4.0 \times 10^5$ peak area or less, $3.0 \times 10^5$ peak area, or less, $2.0 \times 10^5$ peak area or less, or $1.0 \times 10^5$ peak area or less, relative to μl of the extract.

The onion of the present invention produced, evaluated, and selected by the methods described above can be cultivated in accordance with a general procedure for relevant onion varieties used.

The onion of the present invention can be produced by a technique involving sexual or asexual reproduction. According to a technique involving sexual reproduction, the onion plant of the present invention is crossed with the second onion plant to obtain seeds, the resulting seeds are cultivated in accordance with a conventional onion cultivation technique to obtain plants, and parts of the resulting plants are obtained. Thus, the onion and a part thereof of the present invention can be produced. According to need, an onion resulting from crossing in which alliinase gene expression is reduced Can be evaluated and selected by the method described above. "Crossing" may be self-fertilization, sib-pollination, back crossing, crossing with the same or different inbred, or group mass crossing. An onion suitable for crossing of interest can be selected as the "second onion." For example, the second onion can be selected from among the same or different inbred varieties or conventional varieties. The onion plant resulting from crossing may be subjected to crossing one or more times in the same procedure to obtain the onion of the present invention. According to a technique involving asexual reproduction, scale leaves are obtained from the onion of the present invention, and plants are obtained via cultivation in accordance with a general onion cultivation procedure. Alternatively, calluses are obtained from the onion of the present invention, the calluses are regenerated into young plants so as to obtain plants. Thus, the onion and a part thereof of the present invention can be produced. In the present invention, an onion having a history of being produced with the use of the onion of the present invention is occasionally referred to as an "offspring" of the onion plant of the present invention. Such "offspring" and a part thereof ate within the scope of the present invention, provided that alliinase gene expression is reduced in such "offspring" compared with the case of existing varieties.

EXAMPLES

Hereafter, the present invention is described in greater detail with reference to the examples, although the scope of the present invention is not limited to these examples.

Example 1

Production of Spring-Sown Onion without Pungency and Tear-Inducing Property (1-1) Production of M1 Onion Bulb About 1,500 seeds (6.08 g) of Super Kita-momiji were introduced into a plastic petri dish with a diameter of 10 cm, and the seeds were irradiated with neon ion beams at 20 Gy, and the mutagenized first-generation seeds were prepared (hereafter referred to as From the resulting M1 seeds, 60 seeds were separated and subjected to the germination test, so as to estimate the rate of germination and the rate of normal development. Specifically, Golden Peatban was introduced into an accompanying plastic tray, and the tray was filled with 700 ml of tap water. 10 to 15 minutes thereafter, 60 seeds were sowed on Golden Peatban that had absorbed all water and swollen to fill the tray. The tray was allowed to stand in that state in a room overnight, it was transferred to a greenhouse (15° C.), and plants were then allowed to grow therein. One month after sowing, the rate of germination was 86.7% and the rate of plants developing the second leaf sheaths was 55.8%.

From the M1 seeds remaining after the germination test, 1,450 seeds were separated and sowed on a cell tray (on March), rearing of seedlings was continued in a vinyl house, and 1,000 seedlings thereof were settled in the field (i.e., an alley) (on May). The subsequent cultivation was conducted in the same procedure as with onion cultivation in Hokkaido. M1 onions (457 bulbs) were harvested (on September).

(1-2) Selection of M1 Onion

[Primary Selection]

a) Functional Evaluation of Broken Tissue in Terms of Level of tear-Inducing Property and Odor of Raw Onion (Sample Preparation)

Brown coats and scales were peeled until all brown portions completely disappeared in the periphery except for the upper end of the bulb. With the use of a knife with a replaceable blade, part of the outermost scales of the peeled onion bulb (about 5 g to 10 g) was peeled to cut in a longitudinal direction of the bulb. When thickness of the cut scales were smaller than about 1 mm, scales located inside thereof were cut and used. The cut scales were further cut in a horizontal direction and the scales were folded, so that the upper end a scale was aligned with the lower end thereof. The folded scales were introduced into a zippered plastic bag (18 cm×20 cm) for household use (the scales were introduced to be positioned substantially in the center of the zippered plastic bag). The zippered plastic bag was closed so as to minimize the amount of the air remaining in the bag. The closed bag was placed on a metal plate and the folded scales were beaten with a rubber hammer in that state (about 15 to 20 seconds), so as to break onion scales until the scales lots their shapes.

(Functional Evaluation)

Immediately after onion scales were broken, the zippered plastic bag was brought close to the face (the nose and the mouth), the start button of the timer clock (with the count up function) was pressed, the zippered plastic bag was opened immediately thereafter, the nose and the mouth were brought close to the plastic bag opening, and functional evaluation was carried out using the 2 indicators described below:

1. whether or not the odor of raw onion when it is broken is sensed; and 2. the time required before tear-inducing property is sensed after raw onion is broken.

Immediately after the functional evaluation, the zippered plastic bag was closed and introduced into a larger plastic bag, so as to prevent the tear-inducing property or odor from diffusion to avoid the influence thereof on the subsequent functional evaluation.

As a result of the functional evaluation, samples exhibiting A weak odor of raw onion or tear-inducing property were determined to be positive samples, the onion bulbs of the positive samples were made identifiable via labeling; and the samples were refrigerated at 10° C. or lower.

(Points to be Noted)

From the viewpoint of prevention of a lachrymatory factor and a odor component from diffusion, sample preparation and functional evaluation were carried out on a bench-top draft, and such procedures were allowed to proceed by wearing rubber gloves so as to prevent the odor from remaining on the hand.

A sample was subjected to functional evaluation: and the next sample was subjected to functional evaluation at least 3 minutes later, so as to prevent the sensitivity from lowering.

(Verification of Functional Evaluation Sensitivity)

While evaluation of the sample onions was continued, non-irradiated onions exhibiting tear-inducing property and commercialized onion varieties with reduced tear-inducing property and odor of raw onion were subjected to similar functional evaluation, and sensitivity was inspected. Prior to the primary selection, separately, whether or not fruit-like onions, salad onions, and Super Kita-momiji could be distinguished from each other when scales thereof were broken was blind-tested, in order to verify the reliability of evaluation and selection on the basis of tear-inducing property and odor of raw onion sensed when breaking scales in sealed bags. As a result, fruit-like onions with reduced tear-inducing property were selected, and it was determined that functional evaluation at the time of tissue breaking was sufficient for primary selection.

(Results of Primary Selection)

As a result of primary selection, 38 onion bulbs with reduced odor of raw onion or tear-inducing property were selected.

[Secondary Selection]

a) Measurement of the Amount of Lachrymatory Factor (LF) Produced in a Solution Containing Broken Scales In the same procedure as with the primary selection, some of the outermost scales were sampled again from the onion bulbs that were determined positive through the primary selection and stored at 10° C. Distilled water was introduced into the zippered plastic bag containing onion scales in an amount the half the weight of the cut scales, and the bag was Zippered so as to minimize the amount of the air remaining in the bag. The onion scales were beaten with a rubber hammer through the zippered plastic bag and broken. (The start button of the timer clock (with the count up function) was pressed when scale breaking was initiated and the duration after the scales were broken was recorded.) After the scales were broken, the zippered plastic bag was shaken so as to gather as much contents as possible to site in the bag, and the plastic bag was pierced with a 1-ml syringe with a needle at a position close to the position where the broken scales were gathered, so as to extract a solution containing broken onion. The needle at the tip of the syringe was replaced with a 0.2-µm or 0.45-µm filter and the extracted solution containing broken onion was filtered. Immediately thereafter, 1 µl of the filtered solution containing the broken onion was sampled in that state using a microsyringe, applied to HPLC, and then inspected in terms of the amount of FL produced. (The duration from the initiation of breaking to application to HPLC was recorded.) The remaining filtrate was placed on ice. After the sample was applied to HPLC, the solution containing broken onion was recovered with the use of a syringe with a needle, and the amount of the resulting solution was recorded.

b) Assay of LFS Activity of a Solution Containing Broken Scales

To the filtrate (10 µl) in which the amount of LF produced was analyzed, 123 µl of 50 mM phosphate buffer (pH 6.5) was mixed. A fraction (20 µl) was separated from the resulting diluent and diluted with 40 µl of 50 mM phosphate buffer (pH 6.5). With the use of 10 µl of the resulting diluent, LFS activity assay was carried out via HPLC in the procedure described below.

[Procedure of LFS Activity Assay]

1. To a fresh Eppendorf tube, 40 µl of garlic alliinase (50 units/ml) was introduced.

2. To the resulting mixture, 10 µl of 1/20 juice (i.e., the diluent prepared above) was added, followed by pipetting 20 times.

3. 20 µl of PRENCSO (20 mg/ml) was further added thereto, followed by pipetting 5 times, and the tube was closed immediately.

4. The timer clock Set for 3 minutes was started.

5. The lid of the Eppendorf tube was opened when the remaining time reached 20 seconds, 1 µl of the solution was sampled with the use of a 10-µl microsyringe when the timer reached the set time (3 minutes), and the solution was introduced into HPLC.

6. An HPLC inlet and a microsyringe were washed with distilled water.

c) Assay of Alliinase Activity in a Solution Containing Broken Scales

LFS activity was assayed using the filtrate in Which the amount of LF produced was analyzed (before dilution) as the alliinase source, and the alliinase activity level was determined based on the LF peak region appearing in HPLC.
[Procedure of Alliinase Activity Assay]
1. To a fresh Eppendorf tube, 20 µl of the filtrate was introduced.
2. To the resulting mixture, 5 µl of rLFS was added, followed by pipetting 20 times.
3. 10 µl of PRENCSO (20 mg/ml) was further added thereto, followed by pipetting 5 times, and the lid of the tube was closed immediately.
4. The timer clock set for 3 minutes was started.
5. The lid of the Eppendorf tube was opened when the remaining time reached 20 seconds, 1 µl of the solution was sampled with the use of a 10-µl microsyringe when the timer reached the set time (3 minutes), and the solution was introduced into HPLC.
6. An HPLC inlet and a microsyringe were washed with distilled water.

d) Conditions for HPLC Analysis

HPLC conditions employed in a) to c) above are described below. Since all assay techniques involve HPLC analysis of the amount of LF production, the same HPLC conditions are employed.
[Conditions for HPLC Analysis]
Column: ODS (SenshuPak ODS, 4.6 mm×25 cm)
Mobile phase: Methanol:0.005% aqueous trifluoroacetic acid=3:7
Detection: 254 nm
Temperature: 35° C.
Flow rate: 0.6 ml/min
(Results of secondary selection)

As a result of secondary selection, 9 Bulbs (Individual Numbers, B0266, B0108, B0277, B0297, B0383, B0317, B0280, and B0258) were selected.

(1-3) Production of M2 Onion Bulb

The selected M1 onions (9 bulbs: B0266, B0108, B0277, B0297, B0383, B0317, B0280, B0258, and B0371) were allowed to self-fertilization. As a result, approximately 350 seeds (71 seeds from B0108, approximately 80 seeds from B0297, approximately 200 seeds from B0280, and a seed from B0371) were obtained (hereafter, referred to as "M2 generation"). The M2 seeds obtained were cultivated in the same procedure as in the case of the M1 seeds and 197 bulbs of M2 onions (18 bulbs from B0108, 73 bulbs front B0297, and, 106 bulbs from B0280) were obtained.

(1-4) Selection of M2 Onion
(Preparation of Analyte Sample)

In order to avoid variations hi the assay or evaluation results occurring due to the sites of plants used as analyte samples, the particular parts of plants described below are used as analyte samples. An onion bulb is divided into two on the plane perpendicular to the vertical axis of the bulb (i.e., the axis connecting the basal plate to the tipper end of an onion bulb) by a distance that is ⅓ to ½ its height from the upper end of the onion bulb, and an analyte sample is obtained from a scale leaf at the center of the cut plane of the upper portion including the upper end or the lower portion including the basal plate (see FIG. 1). Onion parts are as described above.

Onion tissues (600 mg) were sampled from the M2 onions in accordance with the method described in the "(Preparation of analyte sample)" section above and introduced into the 2-ml Eppendorf safe-lock tube containing 3 zirconia balls (φ: 3 mm). Distilled water (0.6 ml) was added, the tissues were broken using a bead mill (MM.300, QIAGEN) at 30 Hz for 2. minutes, and this procedure was repeated 3 times. The broken onion tissue sample (10 µl) was added to wells of an ELISA plate. The ELISA plate containing the samples was allowed to stand in an incubator adjusted to 37° C. for 1 hour. Thereafter, the ELISA plate was removed from the incubator and then washed in the procedure described below: (i) the solution was removed from all wells; (ii) wash buffer (0.05% polyoxyethylene (20) sorbitan monolaurate (Tween 20-equivalent) in 140 mM NaCl, 10 mM $Na_2HPO_4$—$NaH_2PO_4$ (pH 7.4)) was added at 300 µl/well, the wash buffer was removed immediately, and this procedure was repeated 3 times; (iii) after the wash buffer was removed 3 times, the ELISA plate was thrown on a laboratory table lined with a paper towel to completely remove the wash buffer from the wells. A blocking solution (1% (w/v) BSA in coating buffer (50 mM sodium carbonate-bicarbonate buffer (pH9.6)) was added to the ELISA plate subjected to the steps of washing (i) to (iii) described above at 300 µl/welt. The ELISA plate was allowed to stand in that state in an incubator adjusted to 37° C. for 1 hour: Thereafter, the steps of washing (i) to (iii) were repeated. The primary antibody (i.e., the anti-alliinase rat antiserum diluted 1,000-fold with dilution buffer (0.1% BSA in 140 mM NaCl, 10 mM $Na_2HPO_4$—$NaH_2PO_4$, pH 7.4)) was added to the washed ELISA plate at 100 µl/well. The ELISA plate was allowed to stand for 3 hours when an incubator adjusted to 37° C. was used, or the plate was allowed to stand overnight (16 to 22 hours) when a refrigerator at 4° C. was used, so as to proceed the reaction with the primary antibody. Thereafter, the ELISA plate was subjected to the steps (i) to (iii) of washing described above. The secondary antibody (i.e., POD conjugated anti-rat IgG whole molecule Sigma A0545 diluted 10,000-fold with dilution buffer) was added to the washed ELISA plate at 200 µl/well. The ELISA plate containing the secondary antibody was allowed to stand in an incubator adjusted to 37° C. for 1 hour. Thereafter, the steps (i) to (iii) of washing were repeated. A color reagent (a TBA ELISA substrate solution, Bio-Rad 172-1066) was added to the washed ELISA plate at 100 µl/well. Immediately thereafter, the color development reaction was allowed to proceed while subjecting the ELISA plate to shake-agitation at 60 rpm in an incubator at 25° C. The absorbance at 650 nm was measured using a microplate reader (Emax Molecular Dynamics) within 10 to 60 minutes after the color reagent was added. Instead of the extracted sample, purified alliinase (produced by the method described in JP 2009-254344 A) was used to prepare a dilution series and the dilution series were used to perform assays in the same procedure, the calibration curve was prepared based on the assay results, and the measured absorbance in the extracted sample was converted into the alliinase concentration. In addition, the total protein level in the extract measured by the Bradford method was converted to the level per ng of the extracted protein.

Based on the selection standard such that the amount of color development via ELISA per extracted protein is 1/10 or lower than that of non-irradiated onions, 18 onion bulbs with lower alliinase protein expression level were selected.

(1-5) Self-Fertilization and Seed Production of Selected M2 Bulbs (Production of M3 Generation)
From May to October
Number of Collected Seeds 3,250 M3 seeds (280 seeds from No. 300, 55 seeds from No. 438, 56 seeds from No. 444, 800 seeds from No. 455, 86 seeds from No. 479, 66 seeds from No. 482, 960 seeds from No. 486, 176 seeds from No. 487, 265 seeds from No. 489, 75 seeds from No. 511, 61 seeds from No. 512, and 367 seeds from No. 515) were obtained.

(1-6) Cultivation of Bulb from M3 Seed
From March to September

From among the 3,250 M3 seeds, 1,078 seeds (100 seeds from No. 300, 55 seeds from No. 438, 56 seeds from No. 444, 100 seeds from No. 455, 86 seeds from No. 479, 66 seeds from No. 482, 100 seeds from No. 486, 176 seeds from No. 487, 100 seeds from No 489, 75 seeds from No. 511, 61 seeds from No. 512, and 100 seeds from No. 515) were cultivated in the same procedure as with M1 and M2 seeds, and 466 M3 onion bulbs (81 bulbs from No 300, 28 bulbs from No. 438, 22 bulbs from No. 444, 74 bulbs from No. 455, 29 bulbs from No. 479, 15 bulbs from No. 482, 67 bulbs from No. 487, 37 bulbs from No. 489, 60 bulbs from No. 511, 4 bulbs from No. 512, and 49 bulbs from No. 515) were obtained.

(1-7) Selection from M3 Onion Bulbs
From November to March

From among the M3 onion bulbs, those with reduced alliinase activity were selected using the amount of PRENCSO remaining after scale leaves were broken as the indicator. The selection standard was 3.26 µmol/g FW or more of the amount of remaining PRENCSO. This selection standard was determined because reduced pungency was recognized when alliinase activity was reduced to 1/40 via functional evaluation when the alliinase activity level and the results of functional evaluation were compared during preliminary examination. The amount of remaining PRENCSO when alliinase activity was reduced to 1/40 (i.e., 3.26 µmol/g) was determined by measuring the amount of remaining PRENCSO when alliinase activity was reduced to 1/40 through the model experiment using a general onion variety (Sapporo-ki, 6 bulbs) cultivated in the same field as the M3 onion bulbs. Scale leaves of some of the selected onions were subjected to functional evaluation to determine the presence or absence of pungency.

These selected bulbs were subjected to functional evaluation and alliinase activity assay using leaves during the cultivation aimed at self-fertilization and seed production, so as to identify characteristic features.

As a result, 9 bulbs in which the amount of remaining PRENCSO was 3.26 µmol/g FW or more (lines #2, #6, #10, #11, #37, #230, #262, #263, and #651) were selected.

(1-8) Self-Fertilization and Seed Production of Selected M3 Bulbs (Production of M4 Generation)
From May to October M4 seeds (1,687 seeds (328 seeds from the line #6, 338 seeds from the line, 0, 13 seeds from the line #230, and 1.008 seeds from the line #263)) were obtained.

Separately, the line #2 was subjected to crossing with the line #6 and 2 seeds were obtained.

(1-9) Cultivation of Bulb from M4 Seed
From March to September

From among the 1,689 M4 seeds, 400 seeds (200 seeds from the line #6 and 200 seeds from the line #10) were cultivated in the same procedure as with M1 to M3 seeds, and 226 M4 onion bulbs (158 seeds from the line #6 and 68 seeds from the line 410) were obtained.

Example 2

Various Measurements (2-1) Measurement of the Amount of Pyruvic Acid Produced when Tissues are Broken Onion tissues (600 mg) ere sampled in accordance with the method described in the "(1-4) Preparation of analyte sample" section above and introduced into the 2-ml Eppendorf safe-lock tube containing 3 zirconia balls (φ: 3 mm). Distilled water (0.6 ml) was added, the tissues were broken using a bead mill (MM300, QIAGEN) at 30 Hz for 2 minutes, and this procedure was repeated 3 times. The resultant was then allowed to stand at room temperature for 10 minutes and then centrifuged at 15,000 rpm and 4° C. for 10 minutes. The supernatant was designated as the sample. The sample (20 µl) was introduced into wells of a 96-well plate, 43 µl of water and 66 µl of a DNPH solution were added 30 minutes after the tissues were broken, and the reaction was allowed to proceed at 37° C. for 10 minutes. Thereafter, 66 µl of 1.5 M NaOH was added to terminate the reaction, followed by mixing with pipetting 3 or more times. The absorbance at 515 nm was assayed using a spectrophotometer. The calibration curve was prepared using the values measured in the same procedure with the use of a dilution series of a sodium pyruvate solution instead of the extracted sample. The measured absorbance of the extracted sample was converted to the amount of pyruvic acid.

(2-2) Measurement of the Amount of PRENCSO Remaining 3 Hours after Tissues are Broken Onion tissues (600 mg) were sampled in accordance with the method described in the "(1-4) Preparation of analyte sample" section above and introduced into the 2-ml Eppendorf safe-lock tube containing 3 zirconia balls (φ: 3 mm). Distilled water (0.6 ml) was added, the tissues were broken using a bead mill (MM300, QTAGEN) at 30 Hz for 2 minutes, and this procedure was repeated 3 times. The resultant was then allowed to stand at room temperature for 3 hours and then centrifuged at 15,000 rpm and 4° C. for 10 minutes. The resulting supernatant was filtered through a 0.45-µm membrane filter and the resultant was designated as the sample. The amount of PRENCSO was measured in accordance with a conventional technique (JP 2009-254344 A).

(2-3) Measurement of the Amount of Lachrymatory Factor (LF) Produced when Tissues are Broken Onion tissues (400 mg) sampled in accordance with the method described in the "Preparation of analyte sample" section above were introduced into a 1.5-ml Eppendorf tube. The tissues were broken using a micropestle for 20 seconds, the broken tissues were centrifuged at 15,000 rpm and 4° C. for 10 seconds immediately thereafter, and the amount of the lachrymatory factor (LF) in 1 µl of the supernatant was analyzed via HPLC 1 minute and 20 seconds after the tissues were broken.

The conditions for HPLC analysis described below were employed. Under such conditions for HPLC analysis, the lachrymatory factor (LF) was detected at the retention time of approximately 9.6 minutes.

[Conditions for HPLC Analysis]
Column: ODS (SenshuPak ODS, 4.6 mm×25 cm)
Mobile phase: Methanol:0.005% aqueous trifluoroacetic acid=3:7
Detection: 254 nm
Column Temperature: 35° C.
Flow rate: 0.6 ml/min (2-4) Measurement of Alliinase Protein Expression Level Via ELISA The onion tissues broken in the same procedure as with the measurement of the amount of pyruvic acid produced were designated as the samples, and the alliinase protein expression levels in the samples were measured by the method similar to ELISA described in the "(1-4) Selection of M2 onion" section above.

(2-5) Measurement of Alliinase Gene Expression Level Via Real-Time PCR

With the use of the RNeasy Plant Mini kit (Qiagen), RNA was extracted from 100 mg of the onion tissues cryopreserved at −80° C. in accordance with the manufacturer's instructions. The concentration of the sampled RNA was measured using NanoDrop 1000 (NanoDrop Technologies), and reverse transcription was carried out using the ReverTra Ace® qPCR RT Master Mix with gDNA Remover (Toyobo Co., Ltd.) in accordance with the manufacturer's instructions, so as to synthesize cDNA. Gene quantification was carried out using the sets of primers shown in the table below and the THUNDERBIRD® SYBR® qPCR Mix (Toyobo Co., Ltd.) in the 7900 HT Fast Real-Time PCR System (Applied Biosystems). The results were corrected with the expression level of a ubiquitin housekeeping gene.

```
Alliinase primers:
Forward primer:
5'-AATGAGACCTCCATCCCCATC-3'      (SEQ ID NO: 1)

Reverse primer:
5'-TCGAAACCCTCTCCACTTTG-3'       (SEQ ID NO: 2)

Ubiquitin primers:
Forward primer:
5'-ACGATTACACTAGAGGTGGAGAGCTC-3' (SEQ ID NO: 3)

Reverse primer:
5'-CCTGCAAATATCAGCCTCTGCT-3'     (SEQ ID NO: 4)
```

(2-6) Data Demonstration and Statistic Analysis

The measured values were represented in terms of "mean±standard deviation," and the statistic analysis was carried out in accordance with the Dunnett's method. Significance levels were indicated at 5% (*) and 1% (**).

Example 3

Results of Various Measurements and Evaluation of M4 Onion Bulb (3-1) Functional Evaluation Samples were obtained from the two lines of M4 onion bulbs (the line #6 and the line #10, 20 bulbs each) and 5 bulbs of the control Sapporo-ki variety in accordance with the method described in the "(1-4) Preparation of analyte sample" section above. At least two panels were asked to evaluate functions by the method described in the "Functional evaluation" section above. That is, the M4 onion bulbs were compared with the control bulbs, and whether or not significant reduction was observed in the degrees of tear-inducing property exhibited when some samples were broken and/or pungency exhibited when some samples were broken or eaten was evaluated. As a result, none of the line #6 or #10 bulbs exhibited pungency (Table 1).

TABLE 1

|  | Number of bulbs subjected to functional evaluation | Number of bulbs exhibiting pungency |
|---|---|---|
| Control | 5 | 5 |
| #6 | 20 | 0 |
| #10 | 20 | 0 |

(3-2) Amount of Pyruvic Acid Produced when Tissues are Broken

In accordance with the method described in the "(2-1) Measurement of the amount of pyruvic acid produced when tissues are broken" section above, the amounts of pyruvic acid produced when the two lines of M4 onion bulbs (the line #6 and the line #10, 19 bulbs each) and the control Sapporo-ki variety (5 bulbs) were broken were measured.

Figure 2:
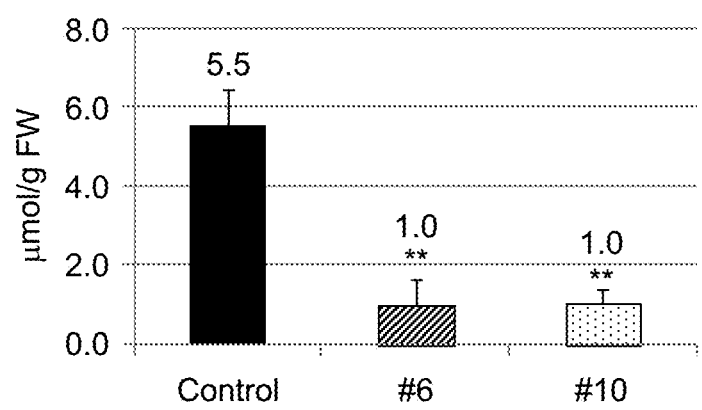
FIG. 2 shows the results of measuring the amount of pyruvic acid produced when the M4 onion bulb tissues are broken.

The results are shown in FIG. 2. In comparison with the control samples, the amount of pyruvic acid produced in the line #6 and the line #10 was significantly reduced. These results were consistent with the results of functional evaluation.

(3-3) Amount of PRENCSO Remaining 3 Hours after Tissues are Broken

In accordance with the method described in the "(2-2) Measurement of the amount of PRENCSO remaining 3 hours after tissues are broken" section above, the samples were obtained from the two lines of M4 onion bulbs (the line #6 and the line #10, 19 bulbs each) and the control Sapporo-ki variety (5 bulbs), and the amounts of PRENCSO remaining 3 hours after the samples were broken were measured.

Figure 3:
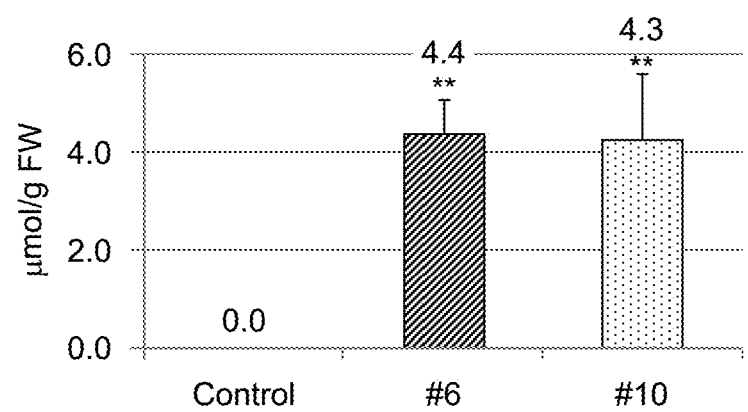
FIG. 3 shows the results of measuring the amount of PRENCSO remaining 3 hours after the M4 onion bulb tissues are broken.

The results are shown in FIG. 3. In comparison with the control samples, PRENCSO was remaining in the line #6 and the line #10. Such onions were not discovered in the past. Also, these results were consistent with the results of functional evaluation and the results of analysis of the amount of pyruvic acid production.

(3-4) Amount of Lachrymatory Factor (LF) Produced when Tissues are Broken

In accordance with the method described in the "(2-3) Measurement of the amount of lachrymatory factor (LF) produced when tissues are broken" section above, the samples were obtained from the two lines of M4 onion bulbs (the line #6 and the line #10, 19 bulbs each) and the control Sapporo-ki variety (5 bulbs), and the amounts of the lachrymatory factor (LF) produced when the samples were broken were measured.

Figure 4:
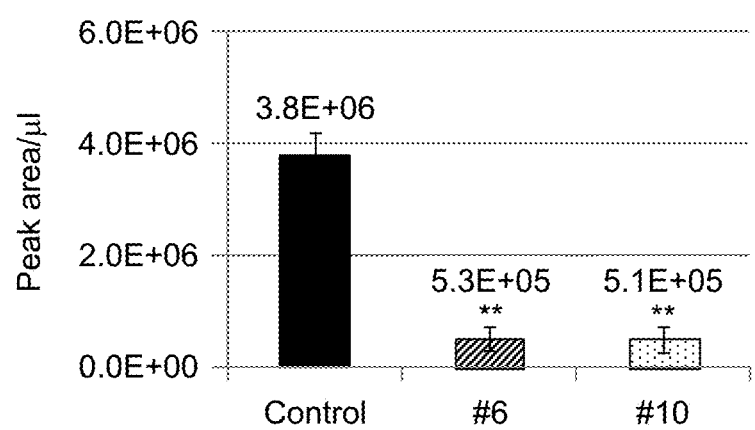
FIG. 4 shows the results of measuring the amount of lachrymatory factor (LF) produced when the M4 onion bulb tissues are broken.

The results are shown in FIG. 4. In comparison with the control samples, the amount of the lachrymatory factor (LF) produced in the line #6 and the line #10 was significantly reduced.

(3-5) Alliinase Protein Expression Level

In accordance with the method described in the "(2-4) Measurement of alliinase protein expression level via ELISA" section above, the samples were obtained from the two lines of M4 onion bulbs (the line #6 and the line #10, 19 bulbs each) and the control Sapporo-ki variety (5 bulbs), and the alliinase protein expression levels were measured via ELISA.

Figure 5:
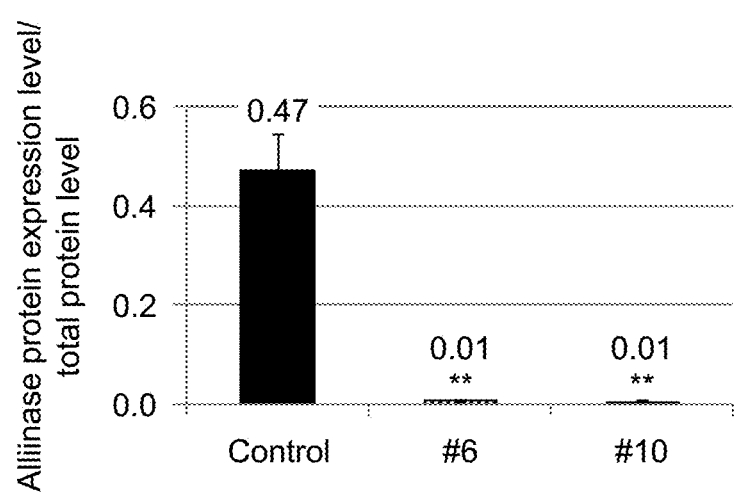
FIG. 5 shows the results of measuring the level of alliinase protein expression of the M4 onion bulb.

The results are shown in FIG. 5. In comparison with the control samples, the alliinase protein expression levels were significantly suppressed in the line #6 and the line #10.

(3-6) Alliinase Gene Expression Level

In accordance with the method described in the "(2-5) Measurement of alliinase gene expression level via real-time PCR" section above, the alliinase gene expression levels in the two lines of M4 onion bulbs (the line #6 and the line #10, 3 bulbs each) and the control Sapporo-ki variety (3 bulbs) were measured via quantitative RT-PCR.

Figure 6:
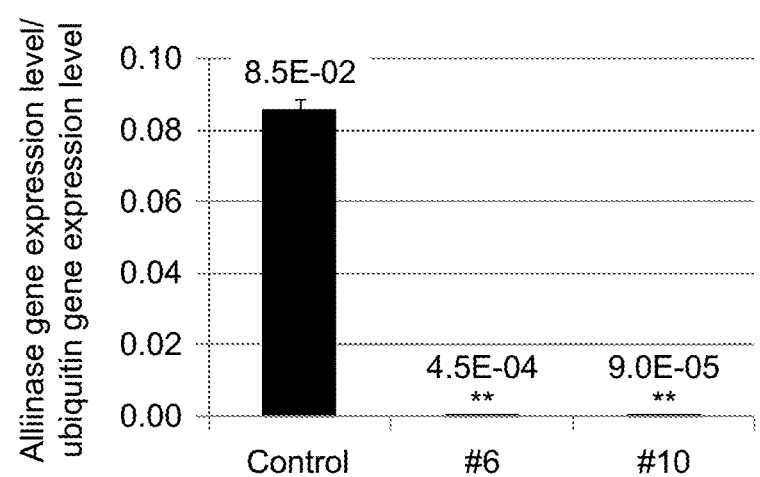
FIG. 6 shows the results of measuring the level of alliinase gene expression of the M4 onion bulb.

The results are shown in FIG. 6 in terms of the proportion of the alliinase gene to the ubiquitin gene. In comparison with the control samples, the proportions of the alliinase gene to the ubiquitin gene in the line #6 and the line #10 were 1/187 and 1/1,000, respectively. Thus, alliinase gene expression was confirmed to have been significantly suppressed.

On the basis of the results described above and the ELISA results demonstrating the reduced alliinase protein expression level, the line #6 and the line #10 were found to be free of pungency because alliinase expression was suppressed therein.

Example 4

Verification of LFS Activity in Line #6 and Line #10

As described in the "(3-4) Amount of lachrymatory factor (LF) produced when tissues are broken" section above, it was confirmed that the amount of LF produced when tissues were broken was significantly suppressed in the line #6 and the line #10. This suggests that LFS activity is suppressed in addition to alliinase activity. Purified alliinase is prepared from a garlic in accordance with a conventional technique (JP 2009-254344 A), and 12.5 units of the obtained purified alliinase were added to the onion tissues of the line #6 and the line #10 obtained in the same procedure as with the "(3-4)" above; the onion tissues were broken, and the amount of a lachrymatory factor (LF) produced was measured in the procedure described above. For comparison, the samples were obtained from the control Sapporo-ki variety (5 bulbs) and the amounts of the lachrymatory factor (LF) produced when the samples were broken were measured by the method described above.

Figure 7:
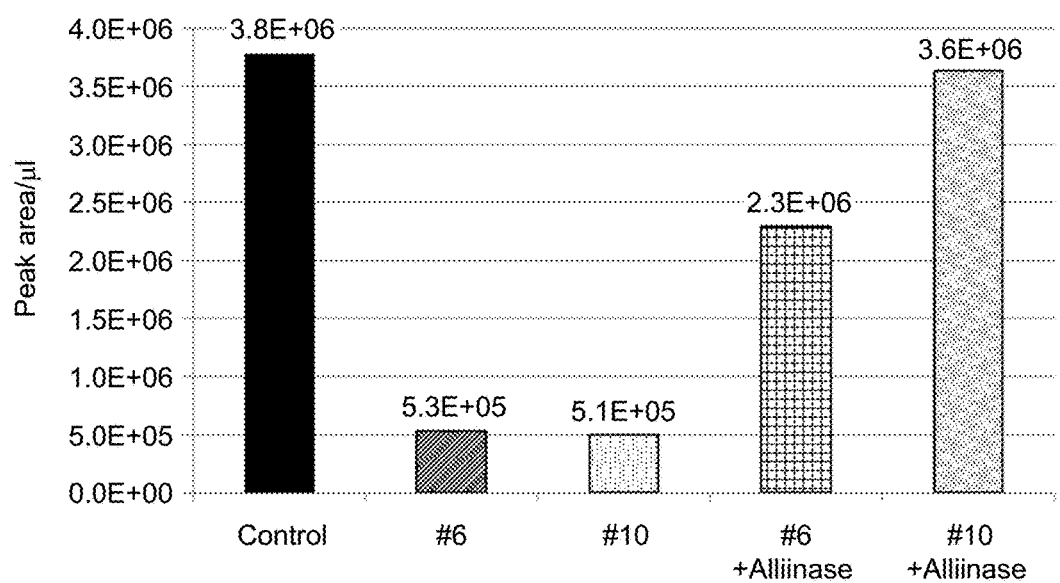
FIG. 7 shows the results of measuring the amount of lachrymatory factor (LF) produced when alliinase is added upon breaking the M4 onion bulb.

The results are shown in FIG. 7. With the addition of alliinase when onion tissue were broken, the amounts of the lachrymatory factor (LF) produced in the line #6 and the line #10 became equivalent to those of the control. These results demonstrate that the amounts of the lachrymatory factor (LF) produced when the line #6 and the line #10 were broken are small because alliinase is suppressed and LF per se functions without problems.

The present inventors designated the seeds obtained from the line #6 as *Allium cepa* HFG-01 and deposited internationally under Accession Number NCIMB 42219 at NCIMB Ltd., Ferguson Building, Craibstone Estate, Bucksbum, Aberdeen AB21 91YA, United Kingdom, on Feb. 19, 2014. The address written in the certificate of deposit is of the development laboratory where the applicant of the present invention Works, and the depositor is the applicant of the present invention.

Example 5

Induction of Callus From M4 Onion Bulb

Figure 8:
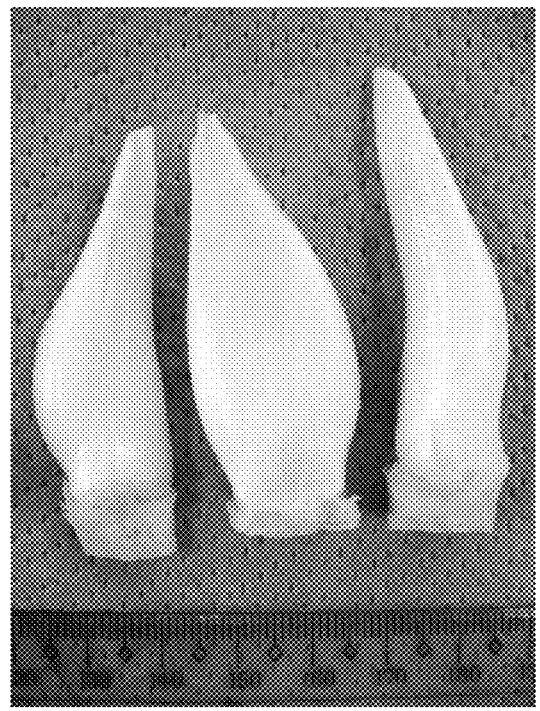
FIG. 8 is a photograph showing the plumules (i.e., developing leaf portions including a basal plate) excised from the central parts of onion bulbs.

The outer leaves of M4 onion bulbs (the line #6) were peeled, the plumule in the center (the developing leaves including the basal plate, FIG. 8) was excised, and it was then sterilized in an aqueous solution of 1% sodium chlorite for 30 minutes. After the sterilized plumule was rinsed twice with sterile water, the regions damaged through sterilization (the outermost leaves and the basal plate) were removed with a surgical knife under aseptic conditions. Thereafter, the developing leaves were cut horizontally into cross sections with a thickness of about 0.5 mm and placed on a callus induction medium. The callus induction medium used herein was Murashige and Skoog medium (hereafter referred to as "MS") containing 50 µM 4-fluorophenoxyacetic acid (hereafter referred to as "4-FPA"), 1 µM N6 (2-isopentenyl) adenine (hereafter referred to as "2iP"), 0.1 M sucrose, 0.1% casein hydrolysate, and 0.2% gellan gum, and a pH thereof was adjusted to 5.8. Culture was conducted at 25° C. in the light for 12 hours (40 mol/m$^2$/s). The cross sections were enlarged 1 week after the initiation of culture, and callus formation was then initiated. Two weeks after the initiation of culture, the enlarged cross sections were cut into pieces of about 5 mm square, and the resulting pieces were placed on new callus induction medium. Two weeks after the initiation of subculture, sufficient callus proliferation was observed, and subculture was performed by transferring the pieces to a fresh callus subculture medium (MS medium containing 50 µM 4-FPA, 1 µM 2iP, 0.1 M sucrose, and 0.3% gellan gum) every 4 to 6 weeks to obtain calluses. The present inventors designated such callus as HFG-01C and deposited the same internationally under Accession Number FERM BP-22260 at the Patent Microorganisms Depositary (NPMD), the National Institute of Technology and Evaluation (NITE) (#120, 2-5-8 Kazusakamatari, Kisarazu-shi, Chiba, 292-0818, Japan) on Dec. 25, 2013.

Example 6

Regeneration from Callus and Production of Plant (1) Regeneration

Figure 9:
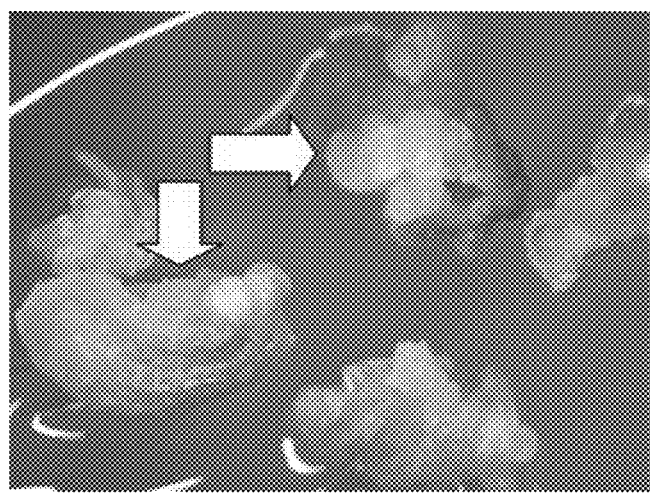
FIG. 9 is a photograph showing culture products obtained via culture of calluses in a regeneration medium. Arrows indicate a smooth-surfaced structure observed in the culture product.

The calluses obtained in Example 5 were cultured in a regeneration medium (MS medium containing 1 µM, 2iP, 0.1 M sucrose, and 0.3% gellan gum) at 25° C. in the light for 12 hours (40 mol/m$^2$/s). Smooth-surfaced structures were observed approximately 1 month after the initiation of culture (FIG. 9). The culture product containing these structures was transferred to a fresh regeneration medium every 4 to 6 weeks. Shoots were differentiated from the culture product that had been transferred to another regeneration medium approximately 2 times.

(2) Rooting

Figure 10:
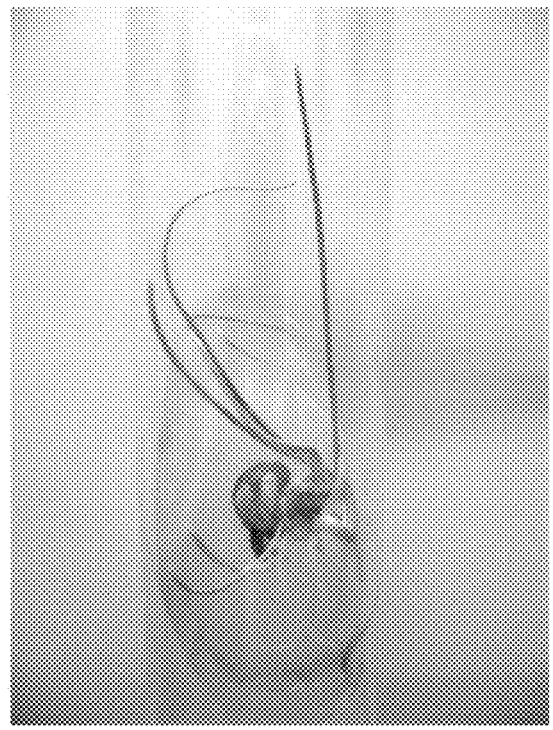
FIG. 10 is a photograph showing plants regenerated from a callus.

The differentiated shoots obtained in (1) were cultured in MS medium containing 0.1 M Sucrose, 0.2% gellan gum, and 0.5% agar at 25° C. in the light for 12 hours (40 µmol/m$^2$/s). Root differentiation was observed 1 month after the initiation of culture (FIG. 10), and plants were thus obtained from calluses.

These results demonstrate that calluses induced from M4 onion bulbs Can: be cultured and grown, and the calluses can be regenerated into plants.

Example 7

Seed Production from M4 Onion Bulb Via Mass Crossing (Production of M5 Generation)

M4 onion bulbs (7 bulbs; line #6) were subjected to mass crossing and 610 M5 seeds were obtained. Separately, 17 M4 onion bulbs (line #10) were subjected to mass crossing and 421 M5 seeds were obtained.

Example 8

Analysis of Alliinase Gene in M4 Onion Bulb (Line #6, Line #10)

In order to find the reason why alliinase gene expression is reduced in the line #6 and the line #10, differences in genes expressed in the onions of line #6 and general onions i.e., those exhibiting pungency and tear-inducing property because alliinase gene expression is not reduced therein) were exhaustively analyzed using a next-generation sequencer by the method described below.

The M4 onion bulbs (3 bulbs; the line #6) and the 3 control onion bulbs of the same variety as the line #6 and exhibiting pungency, which had been subjected to self-fertilization the same number of times as the line #6, were rapidly frozen in liquid nitrogen and then cryopreserved at −80° C.

Frozen onion bulbs were peeled, 100 mg of onion tissues was fractionated, and total RNA was extracted therefrom using the RiNeasy Plant Mini kit (Qiagen) in accordance with the instructions. The total RNA was subjected DNase treatment using the RNeasy Mini Kit (Qiagen) and the RNase-Free DNase Set (Qiagen). After the treatment, total RNA was subjected to measurement of the concentration and quality verification using Nanodrop (Nanodrop Technologies) and Agilent 2100 Bioanalyzer (Aglent Technologies). Through quality verification, it was confirmed that the sample exhibited A260/A280 of 1.8 or more and the RNA integrity number of 8.0 or more, and a sequence library was prepared using the TruSeq RNA Sample Prep Kit (Illumina) in accordance with the manufacturer's instructions. The prepared sequence library was subjected to sequence analysis using a next-generation sequence (HiSeq, Illumina) under the conditions described below.

(Sequencing Conditions)
Method of analysis: Paired-end; the number of analytes: 6; the number of lanes: 3; the number of nucleotides to be read: 100 nucleotides/read (Data Processing)
The obtained data were processed in the procedure described below.

A calculation formula referred to as a "chastity" was used to eliminate the data with a low fluorescent purity. "Chastity" is represented by a formula I1/(I1+I2) in which "I1" represents the maximal signal emitted from 4 types of nucleotides and "I2" represents the subsequent signal. In this example, data were selected under the conditions of I1/(I1+I2)>0.6.

The selected data were classified based on the analyte-specific index information for each analyte.

Read sequences comprising adaptor sequences were removed, and a pair of reads containing 90% or more nucleotides exhibiting the quality value of 20 or higher was extracted. All the data for the analytes were used to conduct de novo assembly using Trinity (world wide web.trinityrnaseq.sourceforge.net/index).

The assembled data (the putative transcript sequence) were annotated by BLAST™ search. BLASTX was employed as the annotation program, and RefSeq-fungi, RefSeq-microbial, and RefSeq-plant (NCBI) and the integrated database comprising the amino acid sequences registered as Allieae in accordance with the NCBI classification, and the gene sequences thereof converted into the amino acid sequences were employed as database.

The BLASTX parameters are as follows: evalue 1E-5/ num_alignments 100/outfmt "6 qseqid sseqid pident length mismatch gapopen qstart qend sstart send evalue bitscore glen slen stitle qcovs qcovhsp". Default conditions were employed.

The data for the analytes were mapped to the putative transcript sequence using Trinity for expression analysis. On the basis of the results of mapping, the gene expression levels were compared between two groups with the use of edgeR, and gene sequences exhibiting differences in expression levels between two groups were extracted. It was determined that there was a significant difference when a p-value was 0.05 or less and the false discovery rate (FDR) was 0.01 or less.

As a result of BLASTX analysis, a total of 29 genes were annotated as alliinases, such as onion alliinase, alliinase-like substances, or alliinase precursors (FIG. 11).

One of these genes was found to be reduced to be expressed in the 3 onion bulbs of the line #6 at a significant level, and it was found to be expressed in the 3 control onion bulbs (hereafter, this alliinase gene is referred to as the "alliinase gene 1" for convenience). FIG. 12 shows the amino acid sequence encoded by the alliinase gene 1.

The alliinase gene 1 (Gene No. 1 in FIG. 11) exhibited the highest expression level among the 29 genes annotated as the alliinases in the control onion bulbs. These results demonstrate that, among the alliinase genes in onion cells, the alliinase gene 1 is the most influential gene on alliinase activity level of onion cells.

To date, 13 types of onion alliinases have been registered at GenBank (e.g., Accession Numbers AAA32639.1 and AAA92463.1). This can result from the fact that there are some differences in nucleotide sequences of various genes among different onion varieties, in addition to the fact that the onion alliinase genes are multicopy genes and that traits of alliinases are different between roots and bulbs of onions (King et al., A low-density genetic map of onion reveals a role for tanden duplication in the evolution of an extremely large diploid genome, Theoretical and Applied Genetics, 96, 52-62, 1998; Do et al., Genomic organization of a novel root alliinase gene, ALL1, in onion, Gene, 325, 17-24, 2004; Masamttra et al., Chromosomal organization and sequence diversity of genes encoding lachrymatory factor synthase in. *Allium cepa* L. Genes/Genomes/Genetics 2: 643-651, 2012).

In addition to the presence of a plurality of the alliinase genes, the degree of influence of each alliinase gene on the alliinase activity level in onion cells is not apparent. When production of onions in which alliinase gene expression is reduced is intended, accordingly, it was not possible to determine the target alliinase gene to be deleted or suppressed. In addition, it was not possible to determine the types of alliinase genes to be deleted or suppressed that were: necessary to effectively delete or inhibit alliinase gene expression. Accordingly, it was difficult to identify the target alliinase genes.

On the basis of the results described above, the alliinase gene that is the most influential on the alliinase activity level in onion cells was identified from among a plurality of alliinase genes existing in the onion genome. In addition, the results demonstrate that onions in which the expression level of the gene of interest (i.e., the alliinase gene 1.) is remarkably low exhibit substantially no pungency.

Specifically, the alliinase gene 1 is the main alliinase gene in an onion bulb, deletion or reduction of the expression of the alliinase gene 1 is sufficient to delete or reduce the expression of the entire alliinase genes in an onion bulb, and pungency and tear-inducing property of an onion can thus be reduced.

All publications, patents, and patent applications cited herein are incorporated herein by reference in their entirety.

The invention claimed is:

1. An onion plant, an offspring, a part of the onion plant, or a part of the offspring,
   wherein a seed of the onion plant is deposited internationally under NCIMB 42219,
   wherein a callus of the onion plant is deposited internationally under FERM BP-22260, and
   wherein the seed of the onion plant that is deposited internationally under NCIMB 42219, the callus of the onion plant that is deposited internationally under FERM BP-22260, the offspring, the part of the onion plant, or the part of the offspring have an alliinase gene disrupted, and
   wherein the alliinase gene comprises a nucleotide sequence encoding a polypeptide comprising the amino acid sequence as shown in SEQ ID NO: 5.

2. An onion plant an offspring, a part of the onion plant, or a part of the offspring obtained from a seed or a callus of the onion plant, wherein the seed is deposited internationally under NCIMB 42219, wherein the callus is deposited internationally under FERM BP-22260, and wherein the seed of the onion plant that is deposited internationally under NCIMB 42219, the callus of the onion plant that is deposited internationally under FERM BP-22260, the offspring, the part of the onion plant, or the part of the offspring have an alliinase gene disrupted, and wherein the alliinase gene comprises a nucleotide sequence encoding a polypeptide comprising the amino acid sequence as shown in SEQ ID NO: 5.

3. An onion plant an offspring, a part of the onion plant, or a part of the offspring that has an alliinase gene disrupted, which is produced by a method comprising crossing a first onion plant with a second onion plant, wherein the first onion plant is an onion plant obtained from a seed deposited internationally under NCIMB 42219 or a callus deposited internationally under FERM BP-22260, wherein the seed of the onion plant that is deposited internationally under NCIMB 42219, the callus of the onion plant that is deposited internationally under FERM BP-22260, the offspring, the part of the onion plant, or the part of the offspring have an alliinase gene disrupted, and wherein the alliinase gene comprises a nucleotide sequence encoding a polypeptide comprising the amino acid sequence as shown in SEQ ID NO: 5.

4. The onion plant, an offspring, a part of the onion plant, or a part of the offspring according to claim 1, which is a part of the onion plant and wherein the part is a bulb.

\* \* \* \* \*

SEQUENCE LISTING

```
<160> NUMBER OF SEQ ID NOS: 5

<210> SEQ ID NO 1
<211> LENGTH: 21
<212> TYPE: DNA
<213> ORGANISM: Artificial
<220> FEATURE:
<223> OTHER INFORMATION: primer

<400> SEQUENCE: 1
aatgagacct ccatccccat c                                              21

<210> SEQ ID NO 2
<211> LENGTH: 20
<212> TYPE: DNA
<213> ORGANISM: Artificial
<220> FEATURE:
<223> OTHER INFORMATION: primer

<400> SEQUENCE: 2
tcgaaaccct ctccactttg                                                20

<210> SEQ ID NO 3
<211> LENGTH: 26
<212> TYPE: DNA
<213> ORGANISM: Artificial
<220> FEATURE:
<223> OTHER INFORMATION: primer

<400> SEQUENCE: 3
acgattacac tagaggtgga gagctc                                         26

<210> SEQ ID NO 4
<211> LENGTH: 22
<212> TYPE: DNA
<213> ORGANISM: Artificial
<220> FEATURE:
<223> OTHER INFORMATION: primer

<400> SEQUENCE: 4
cctgcaaata tcagcctctg ct                                             22

<210> SEQ ID NO 5
<211> LENGTH: 479
<212> TYPE: PRT
<213> ORGANISM: Allium cepa

<400> SEQUENCE: 5

Met Glu Ser Tyr His Lys Val Gly Ser Asn Lys Met Pro Ser Leu Leu
1               5                  10                  15

Ile Leu Ile Cys Ile Ile Met Ser Ser Phe Val Asn Asn Ile Ala
            20                  25                  30

Gln Ala Lys Val Thr Trp Ser Leu Lys Ala Ala Glu Glu Ala Glu Ala
        35                  40                  45

Val Ala Asn Ile Asn Cys Ser Gly His Gly Arg Ala Phe Leu Asp Gly
    50                  55                  60

Ile Leu Ser Asp Gly Ser Pro Lys Cys Glu Cys Asn Thr Cys Tyr Thr
65                  70                  75                  80

Gly Ala Asp Cys Ser Glu Lys Ile Thr Gly Cys Ser Ala Asp Val Ala
                85                  90                  95

Ser Gly Asp Gly Leu Phe Leu Glu Glu Tyr Trp Gln Gln His Lys Glu
            100                 105                 110
```

```
Asn Ser Ala Val Leu Val Ser Gly Trp His Arg Met Ser Tyr Phe Phe
            115                 120                 125

Asn Pro Val Ser Asn Phe Ile Ser Phe Glu Leu Glu Lys Thr Ile Lys
        130                 135                 140

Glu Leu His Glu Ile Val Gly Asn Ala Ala Lys Asp Arg Tyr Ile
145                 150                 155                 160

Val Phe Gly Val Gly Val Thr Gln Leu Ile His Gly Leu Val Ile Ser
                165                 170                 175

Leu Ser Pro Asn Met Thr Ala Thr Pro Cys Ala Pro Gln Ser Lys Val
            180                 185                 190

Val Ala His Ala Pro Tyr Tyr Pro Val Phe Arg Glu Gln Thr Lys Tyr
            195                 200                 205

Phe Asp Lys Lys Gly Tyr Glu Trp Lys Gly Asn Ala Ala Asp Tyr Val
        210                 215                 220

Asn Thr Ser Thr Pro Glu Gln Phe Ile Glu Met Val Thr Ser Pro Asn
225                 230                 235                 240

Asn Pro Glu Gly Leu Leu Arg His Glu Val Ile Lys Gly Cys Lys Ser
                245                 250                 255

Ile Tyr Asp Met Val Tyr Tyr Trp Pro His Tyr Thr Pro Ile Lys Tyr
            260                 265                 270

Lys Ala Asp Glu Asp Ile Met Leu Phe Thr Met Ser Lys Tyr Thr Gly
        275                 280                 285

His Ser Gly Ser Arg Phe Gly Trp Ala Leu Ile Lys Asp Glu Thr Val
        290                 295                 300

Tyr Asn Lys Leu Leu Asn Tyr Met Thr Lys Asn Thr Glu Gly Thr Ser
305                 310                 315                 320

Arg Glu Thr Gln Leu Arg Ser Leu Lys Ile Leu Lys Glu Val Ile Ala
                325                 330                 335

Met Val Lys Thr Gln Lys Gly Thr Met Arg Asp Leu Asn Thr Phe Gly
            340                 345                 350

Phe Gln Lys Leu Arg Glu Arg Trp Val Asn Ile Thr Ser Leu Leu Asp
        355                 360                 365

Lys Ser Asp Arg Phe Ser Tyr Gln Lys Leu Pro Gln Ser Glu Tyr Cys
370                 375                 380

Asn Tyr Phe Arg Arg Met Arg Pro Pro Ser Pro Ser Tyr Ala Trp Val
385                 390                 395                 400

Lys Cys Glu Trp Glu Glu Asp Lys Asp Cys Tyr Gln Thr Phe Gln Asn
                405                 410                 415

Gly Arg Ile Asn Thr Gln Ser Gly Glu Gly Phe Glu Ala Gly Ser Arg
            420                 425                 430

Tyr Val Arg Leu Ser Leu Ile Lys Thr Lys Asp Asp Phe Asp Gln Leu
        435                 440                 445

Met Tyr Tyr Leu Lys Asn Met Val Glu Ala Lys Arg Lys Thr Pro Leu
    450                 455                 460

Ile Lys Gln Leu Ser Asn Asp Gln Ile Ser Arg Arg Pro Phe Ile
465                 470                 475
```